United States Patent
Perni et al.

(10) Patent No.: US 11,912,680 B2
(45) Date of Patent: Feb. 27, 2024

(54) NITRIC OXIDE RELEASING PRODRUGS OF MDA AND MDMA

(71) Applicant: ATAI Life Sciences AG, Berlin (DE)

(72) Inventors: Robert B. Perni, Marlborough, MA (US); Glenn Short, Scituate, MA (US); Tanweer A. Khan, Bridgewater, NJ (US)

(73) Assignee: EmpathBio, Inc., Encinitas, CA (US)

( * ) Notice: Subject to any disclaimer, the term of this patent is extended or adjusted under 35 U.S.C. 154(b) by 0 days.

(21) Appl. No.: 18/147,189

(22) Filed: Dec. 28, 2022

(65) Prior Publication Data

US 2023/0227421 A1 Jul. 20, 2023

Related U.S. Application Data

(60) Provisional application No. 63/294,225, filed on Dec. 28, 2021.

(51) Int. Cl.
| | | |
|---|---|---|
| *C07D 307/79* | (2006.01) | |
| *C07D 317/58* | (2006.01) | |
| *C07D 319/18* | (2006.01) | |

(52) U.S. Cl.
CPC ......... *C07D 317/58* (2013.01); *C07D 307/79* (2013.01); *C07D 319/18* (2013.01)

(58) Field of Classification Search
CPC .................................................. C07D 307/79
See application file for complete search history.

(56) References Cited

U.S. PATENT DOCUMENTS

| | | | |
|---|---|---|---|
| 3,907,864 | A | 9/1975 | Biel et al. |
| 4,017,636 | A | 4/1977 | Jones et al. |
| 4,937,360 | A | 6/1990 | Liu et al. |
| 5,061,727 | A | 10/1991 | Bloom et al. |
| 5,932,749 | A | 8/1999 | Li et al. |
| 9,907,812 | B2 | 3/2018 | Bapat et al. |
| 2003/0171303 | A1 | 9/2003 | Gallop et al. |
| 2003/0207884 | A1 | 11/2003 | Haap et al. |
| 2005/0130244 | A1 | 6/2005 | Zheng et al. |
| 2006/0035863 | A1 | 2/2006 | Barbeau |
| 2006/0205779 | A1 | 9/2006 | Mu et al. |
| 2006/0205946 | A1 | 9/2006 | Ji et al. |
| 2007/0027208 | A1 | 2/2007 | Caron et al. |
| 2008/0045588 | A1 | 2/2008 | Gant et al. |
| 2008/0146567 | A1 | 6/2008 | Kolczewski et al. |
| 2008/0293695 | A1 | 11/2008 | Bristol et al. |
| 2009/0111741 | A1 | 4/2009 | Aldrich et al. |
| 2010/0137428 | A1 | 6/2010 | Bozzoli et al. |
| 2018/0243241 | A1 | 8/2018 | Popp et al. |
| 2021/0145851 | A1 | 5/2021 | Stamets |
| 2021/0332012 | A1 | 10/2021 | Olson et al. |
| 2022/0151986 | A1 | 5/2022 | Liechti et al. |
| 2022/0267252 | A1 | 8/2022 | Trachsel et al. |
| 2022/0354822 | A1 | 11/2022 | Barrow et al. |

(Continued)

FOREIGN PATENT DOCUMENTS

| | | |
|---|---|---|
| CN | 101822841 A | 9/2010 |
| EP | 2687854 A1 | 1/2014 |

(Continued)

OTHER PUBLICATIONS

Anderson, et al., Absolute configuration and psychotomimetic activity, NIDA Res Monogr, 1978, vol. (22), pp. 8-15.

Baker, et al., Critical evaluation of methodology commonly used in sample collection, storage and preparation for the analysis of pharmaceuticals and illicit drugs in surface water and wastewater by solid phase extraction and liquid chromatography-mass spectrometry, Journal of Chromatography A, 2011, pp. 8036-8059.

Baker, et al., Drugs of abuse in wastewater and suspended particulate matter—Further developments in sewage epidemiology, Environment International, 2012, pp. 28-38.

Baker, et al., Multi-residue analysis of drugs of abuse in wastewater and surface water by solid-phase extraction and liquid chromatography-positive electrospray ionisation tandem mass spectrometry, Journal of Chromatography A, 2011, pp. 1620-1631.

(Continued)

*Primary Examiner* — Matthew P Coughlin
(74) *Attorney, Agent, or Firm* — COOLEY LLP

(57) ABSTRACT

Provided herein are compounds of Formula (I), Formula (II), and Formula (III) or pharmaceutically acceptable salt thereof, wherein $R_1$, $R_2$, $R_3$, $R_4$, $R_5$, $R_6$, $R_7$ and A are defined herein. Also provided herein are pharmaceutical compositions comprising a compound of Formula (I), Formula (II), or Formula (III) and methods of using a compound of Formula (I), Formula (II), or Formula (III), e.g., in the treatment of a mental health disease or disorder.

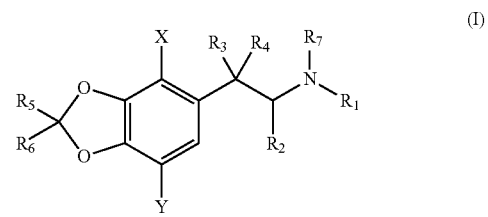

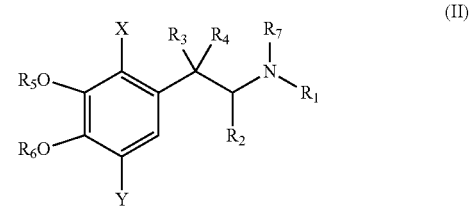

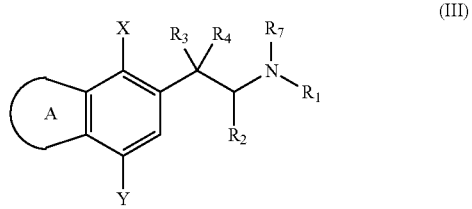

62 Claims, No Drawings

(56) References Cited

U.S. PATENT DOCUMENTS

| | | | |
|---|---|---|---|
| 2023/0096116 | A1 | 3/2023 | Fawaz et al. |
| 2023/0097530 | A1 | 3/2023 | Short et al. |
| 2023/0109467 | A1 | 4/2023 | Anzalone et al. |
| 2023/0129723 | A1 | 4/2023 | Short et al. |
| 2023/0227420 | A1 | 7/2023 | Rao et al. |

FOREIGN PATENT DOCUMENTS

| | | | | |
|---|---|---|---|---|
| WO | WO-2005038049 | A2 | 4/2005 | |
| WO | WO-2007090733 | A1 * | 8/2007 | ............ A61P 29/00 |
| WO | WO-2008033351 | A2 | 3/2008 | |
| WO | WO-2009049233 | A1 | 4/2009 | |
| WO | WO-2009095479 | A2 | 8/2009 | |
| WO | WO-2012177986 | A2 | 12/2012 | |
| WO | WO-2014013063 | A1 | 1/2014 | |
| WO | WO-2017147375 | A1 | 8/2017 | |
| WO | WO-2020077217 | A1 | 4/2020 | |
| WO | WO-2020101543 | A1 | 5/2020 | |
| WO | WO-2020252384 | A1 | 12/2020 | |
| WO | WO-2021252538 | A2 | 12/2021 | |
| WO | WO-2022006192 | A1 | 1/2022 | |
| WO | WO-2022010937 | A1 | 1/2022 | |
| WO | WO-2022032147 | A1 | 2/2022 | |
| WO | WO-2022061242 | A1 | 3/2022 | |
| WO | WO-2022106947 | A1 | 5/2022 | |
| WO | WO-2022150525 | A1 | 7/2022 | |
| WO | WO-2022182602 | A2 | 9/2022 | |
| WO | WO-2022235530 | A1 | 11/2022 | |
| WO | WO-2022256720 | A2 | 12/2022 | |
| WO | WO-2023034510 | A1 | 3/2023 | |
| WO | WO-2023044027 | A1 | 3/2023 | |
| WO | WO-2023056102 | A1 | 4/2023 | |
| WO | WO-2023056472 | A1 | 4/2023 | |
| WO | WO-2023129958 | A2 | 7/2023 | |

OTHER PUBLICATIONS

Baker, et al., Multi-residue determination of the sorption of illicit drugs and pharmaceuticals to wastewater suspended particulate matter using pressurized liquid extraction, solid phase extraction and liquid chromatography coupled with tandem mass spectrometry, Journal of Chromatography A, Nov. 2011, pp. 7901-7913, abstract, 1 page.
Barreiro, J.C., et al., A High-Resolution Magic Angle Spinning NMR Study of the Enantiodiscrimination of 3,4-Methylenedioxymethamphetamine (MDMA) by an Immobilized Polysaccharide-Based Chiral Phase, PLoS One, vol. 11, No. 9, Sep. 26, 2016, pp. 1-11.
Castrignano, et al., Enantiomeric profiling of chiral drug biomarkers in wastewater with the usage of chiral liquid chromatography coupled with tandem mass spectrometry, Journal of chromatography A, Mar. 2016, pp. 84-99.
Castrignano, et al., Enantiomeric profiling of chiral illicit drugs in a pan-European study, Water Research, Mar. 2017, 56 pages.
Chen, et al., Investigation of the relationship between phenol ionization and affinity of norepinephrine for adrenergic receptors using ring-fluorinated analogs, Medicinal Chemistry Research, 1994, pp. 589-597, abstract, 1 page.
Chen, et al., Syntheses of 2,5- and 2,6-difluoronorepinephrine, 2,5-difluoroepinephrine, and 2,6-difluorophenylephrine: effect of disubstitution with fluorine on adrenergic activity, Journal of Medicinal Chemistry, 1993, pp. 3947-3955, abstract, 1 page.
Clouting, H., The Commercial Chemistry of MDMA: From Research to Patient Access, MAPS Bulletin Special Edition, Spring 2020, pp. 8-10.
Collins, et al., Identification and characterization of N-tert-butoxycarbonyl-MDMA: a new MDMA precursor, Drug Testing and Analysis, Mar. 2017, pp. 399-404.
Corkery, et al., Deaths in the Lesbian, Gay, Bisexual and Transgender United Kingdom Communities Associated with GHB and Precursors, Current drug metabolism, Nov. 2018, pp. 1086-1099.
Crean, R.D., et al., Oral Administration of (±)3,4-Methylenedioxymethamphetamine and (+) Methamphetamine Alters Temperature and Activity in Rhesus Macaques, Pharmacol Biochem Behav, vol. 87, No. 1, Authors Manuscript PMC May 1, 2008, pp. 1-18.
Curry et al., Separating the agony from ecstasy: R(−)-3,4-methylenedioxymethamphetamine has prosocial and therapeutic-like effects without signs of neurotoxicity in mice, Neuropharmacology. Jan. 2018; 128: 196-206, 26 pages.
Deluca, et al., Searching the Internet for drug-related web sites: analysis of online available information on ecstasy (MDMA), American Journal on Addictions, Nov. 2007, 5 pages.
Dunlap et al., Dark Classics in Chemical Neuroscience: 3,4-Methylenedioxymethamphetamine (MDMA), ACS Chem Neurosci. Oct. 17, 2018; 9(10): 2408-2427, 46 pages.
Eiden, et al., VMAT2: a dynamic regulator of brain monoaminergic neuronal function interacting with drugs of abuse, Ann N Y Acad Sci., Jan. 2011, pp. 86-98.
Fallon et al., Stereospecific Analysis and Enantiomeric Disposition of 3,4-Methylenedioxymethamphetamine (Ecstasy) in Humans, Clinical Chemistry (1999) 45:7, 1058-1069.
Fantegrossi, et al., 3, 4-Methylenedioxymethamphetamine (MDMA, "ecstasy") and its stereoisomers as reinforcers in rhesus monkeys: serotonergic involvement, Psychopharmacology, Jun. 2002, pp. 56-64.
Fantegrossi et al., Pharmacological characterization of the effects of 3,4-methylenedioxymethamphetamine ("ecstasy") and its enantiomers on lethality, core temperature, and locomotor activity in singly housed and crowded mice, Psychopharmacology (2003) 166: 202-211.
Fantegrossi, In vivo pharmacology of MDMA and its enantiomers in rhesus monkeys, Experimental and clinical psychopharmacology, Feb. 2008, 1 page.
Felim et al., Synthesis and in Vitro Cytotoxicity Profile of the R-Enantiomer of 3,4-Dihydroxymethamphetamine (R-(−)-HHMA): Comparison with Related Catecholamines, Chem. Res. Toxicol. 2010, 23, 211-219.
Filler, et al., Fluorine-containing catecholamines. Synthesis of DL-2,5,6-trifluorodopa, Journal of Fluorine Chemistry, 1981, pp. 483-495.
Fitzgerald, et al., Stereoselective pharmacokinetics of 3, 4-methylenedioxymethamphetamine in the rat, Chirality, 1990, pp. 241-248.
Forsling, et al., The effect of 3,4-methylenedioxymethamphetamine (MDMA,'ecstasy') and its metabolites on neurohypophysial hormone release from the isolated rat hypothalamus, British Journal of Pharmacology, Feb. 2002, pp. 649-656.
Green et al., The pharmacology and clinical pharmacology of 3,4-methylenedioxymethamphetamine (MDMA, "ecstasy"), Pharmacol Rev, Sep. 2003; 55(3): 463-508. Epub Jul. 17, 2003.
Hagele, et al., Enantioselective separation of Novel Psychoactive Substances using a Lux® AMP 3 μm column and HPLC-UV. Journal of Pharmaceutical and Biomedical Analysis, Feb. 2020, 2 pages.
Han, et al., Comparison of the monoamine transporters from human and mouse in their sensitivities to psychostimulant drugs, BMC Pharmacology, Dec. 2006, pp. 1-7.
Heather, E., The Synthesis and Chemical Profiling of 3,4-Methylenedioxymethamphetamine (MDMA) and Analogues, Thesis, University of Technology Sydney, Oct. 2020, 232 pages.
Hensley, et al., Simultaneous determination of amphetamine, methamphetamine, methylenedioxyamphetamine (MDA), methylenedioxymethamphetamine (MDMA), and methylenedioxyethylamphetamine (MDEA) enantiomers by GC-MS, Journal of Analytical Toxicology, Oct. 1999, pp. 518-523.
Herr, et al., Re-evaluation of the discriminative stimulus effects of lysergic acid diethylamide with male and female Sprague-Dawley rats, Behavioral Pharmacology, Sep. 2020, pp. 776-786.
Hiramatsu, et al., Enantiomeric differences in the effects of 3, 4-methylenedioxymethamphetamine on extracellular monoamines and metabolites in the striatum of freely-moving rats: an in vivo microdialysis study, Neuropharmacology, Mar. 1990, pp. 269-275.
Huot et al., Characterization of 3,4-Methylenedioxymethamphetamine (MDMA) Enantiomers In Vitro and in the MPTP-Lesioned Primate:

(56) References Cited

OTHER PUBLICATIONS

R-MDMA Reduces Severity of Dyskinesia, Whereas S-MDMA Extends Duration of ON-Time, The Journal of Neuroscience, May 2011, pp. 7190-7198.
International Search Report and Written Opinion for Application No. PCT/US2022/042353, dated Dec. 8, 2022, and dated Dec. 13, 2022, 9 pages.
International Search Report and Written Opinion for International Application No. PCT/US2022/043833 dated Jan. 12, 2023, 13 pages.
International Search Report and Written Opinion for International Application No. PCT/US2022/082468, dated Jun. 6, 2023, 11 pages.
Invitation to Pay Fee for International Application No. PCT/US2022/045587 dated Nov. 18, 2022, 3 pages.
Invitation to Pay for International Application No. PCT/US2022/082468 dated Mar. 16, 2023, 2 pages.
Johnson et al., Effects of enantiomers of MDA, MDMA and related analogues on [3H] serotonin and [3H] dopamine release from superfused rat brain slices, European Journal of Pharmacology, 1986, pp. 269-276.
Kilpatrick, et al., National estimates of exposure to traumatic events and PTSD prevalence using DSM-IV and DSM-5 criteria, Journal of Traumatic Stress, Oct. 2013, pp. 537-547.
Kozma, D., et al., Optical resolution of N-methylamphetamine via diastereoisomeric salt formation with 2R,3R-O,O'-di-p-toluoyltartaric acid, Chirality, 1999, vol. 11, Issue 5-6, pp. 373-375.
Ladd, et al., Improved synthesis of fluoroveratroles and fluorophenethylamines via organolithium reagents, Journal of Organic Chemistry, 1981, pp. 203-206.
Leapman, et al., Application of parallel recorded EELS to analysis of beam-sensitive organic compounds, Biomed. Eng. Instrum., Proceedings—Annual Meeting, Electron Microscopy Society of America, 1988, pp. 632-633.
Leapman, et al., Applications of electron energy loss spectroscopy in biology: detection of calcium and fluorine, Proceedings—Annual Meeting, Electron Microscopy Society of America, 1982, pp. 412-415.
Levine et al. (editor), Principles of Forensic Toxicology, Springer, Fifth Edition, 2020, 680 pages.
Liabres et al., Molecular basis of the selective binding of MDMA enantiomers to the alpha4beta2 nicotinic receptor subtype: synthesis, pharmacological evaluation and mechanistic studies, European Journal of Medicinal Chemistry, Jun. 2014, pp. 35-46.
Lourenco et al., Chiral separation of 3,4-methylenedioxymethamphetamine (MDMA) enantiomers using batch chromatography with peak shaving recycling and its effects on oxidative stress status in rat liver, Journal of Pharmaceutical and Biomedical Analysis, Jan. 2013, pp. 13-17.
Madry, et al., Evaluation of drug incorporation into hair segments and nails by enantiomeric analysis following controlled single MDMA intakes, Analytical and Bioanalytical Chemistry, Jan. 2016, pp. 545-556.
Martins, et al., Simultaneous enantioselective determination of amphetamine and congeners in hair specimens by negative chemical ionization gas chromatography-mass spectrometry, Journal of Chromatography B, Oct. 15, 2005, pp. 57-62.
Martins, et al., Time-resolved hair analysis of MDMA enantiomers by GC/MS-NCI, Forensic Science International, Oct. 2007, pp. 150-155.
Mas, et al., Cardiovascular and neuroendocrine effects and pharmacokinetics of 3, 4-methylenedioxymethamphetamine in humans, Journal of Pharmacology and Experimental Therapeutics, Jul. 1, 1999, pp. 136-145.
Matsushima, et al., Optical isomer analysis of 3,4-methylenedioxyamphetamine analogues and their stereoselective disposition in rats, Journal of Analytical Toxicology, Jan. 1998, pp. 33-39.
Milhazes, et al., Electrochemical and spectroscopic characterisation of amphetamine-like drugs: Application to the screening of 3,4-methylenedioxymethamphetamine (MDMA) and its synthetic precursors, Analytica Chimica Acta, 2007, pp. 231-241.
Murnane, et al., Discriminative stimulus effects of psychostimulants and hallucinogens in S (+)-3, 4-methylenedioxymethamphetamine (MDMA) and R (−)-MDMA trained mice, Journal of Pharmacology and Experimental Therapeutics, Nov. 1, 2009, pp. 717-723.
Murnane, et al., Endocrine and neurochemical effects of 3, 4-methylenedioxymethamphetamine and its stereoisomers in rhesus monkeys, Journal of Pharmacology and Experimental Therapeutics, Aug. 1, 2010, pp. 642-650.
Murnane, et al., The neuropharmacology of prolactin secretion elicited by 3, 4-methylenedioxymethamphetamine ("ecstasy"): a concurrent microdialysis and plasma analysis study, Hormones and behavior, Feb. 1, 2012, pp. 181-190.
Mustafa, et al., Review Paper: MDMA and the Brain: A Short Review on the Role of Neurotransmitters in Neurotoxicity, Basic and Clinical Neuroscience, 2020, pp. 381-388.
Nair et al., Fully Validated, Multi-Kilogram cGMP Synthesis of MDMA, ACS Omega, Dec. 20, 2021, vol. 7, 1, pp. 900-907.
Nenajdenko et al., A new convenient approach to chiral β-aryl(heteroaryl)alkylamines, Tetrahedron: Asymmetry (2001) 12: 2517-2527.
Nichols, D.E., et al., Derivatives of 1-(1,3-benzodioxol-5-yl)-2-butanamine: representatives of a novel therapeutic class, Journal of Medicinal Chemistry, Oct. 1986, vol. 29 (10), pp. 2009-2015.
Nie, et al., Synthesis of fluorodopamines: effect of aryl fluoro substituents on affinities for adrenergic and dopaminergic receptors, Medicinal Chemistry Research, Jan. 1996, pp. 318-332, abstract, 1 page.
Organic Chemistry Portal, Amino Protecting Groups Stability, (1999), pp. 1-3.
Peters, et al., Concentrations and ratios of amphetamine, methamphetamine, MDA, MDMA, and MDEA enantiomers determined in plasma samples from clinical toxicology and driving under the influence of drugs cases by GC-NICI-MS, Journal of Analytical Toxicology, Nov. 1, 2003, pp. 552-559.
Peters, et al., Drug testing in blood: validated negative-ion chemical ionization gas chromatographic-mass spectrometric assay for determination of amphetamine and methamphetamine enantiomers and its application to toxicology cases, Clinical Chemistry, Sep. 1, 2002, pp. 1472-1485.
Peters, et al., Negative-ion chemical ionization gas chromatography-mass spectrometry assay for enantioselective measurement of amphetamines in oral fluid: application to a controlled study with MDMA and driving under the influence cases, Clinical chemistry, Apr. 1, 2007 A, pp. 702-710.
Pitts et al., (±)-MDMA and its enantiomers: potential therapeutic advantages of R(−)-MDMA, Psychopharmacology, 2018, pp. 377-392.
Pizarro, et al., Stereochemical analysis of 3, 4-methylenedioxymethamphetamine and its main metabolites in human samples including the catechol-type metabolite (3, 4-dihydroxymethamphetamine), Drug Metabolism and Disposition, Sep. 1, 2004, pp. 1001-1007.
Pizarro et al., Synthesis and Capillary Electrophoretic Analysis of Enantiomerically Enriched Reference Standards of MDMA and its Main Metabolites, Bioorganic & Medicinal Chemistry (2002) 10: 1085-1092.
Pubchem, SID 235735835, Feb. 13, 2015, 8 pages.
Pubchem, SID 243280603, Mar. 16, 2015, 7 pages.
Pubchem, Substance Record for SID 104098418, Jan. 2011, 6 pages.
PubChem, Substance Record for SID 117678335, Apr. 2011, 6 pages.
Pubchem, Substance Record for SID 38492237, Dec. 5, 2007, 5 pages.
Pubchem, Substance Record for SID 406789554, Jul. 18, 2020, 6 pages.
Pubchem, Substance Record for SID 439624087, Jan. 15, 2021, 6 pages.
Pubill, et al., Neuronal nicotinic receptors as new targets for amphetamine-induced oxidative damage and neurotoxicity, Pharmaceuticals, Jun. 15, 2011, pp. 822-847.

(56) References Cited

OTHER PUBLICATIONS

Rasmussen et al., Chiral separation and quantification of R/S-amphetamine, R/S-methamphetamine, R/S-MDA, R/S-MDMA, and R/S-MDEA in whole blood by GC-EI-MS, Journal of Chromatography B, (2006) 842: 136-141.
Rickli, et al., Pharmacological profile of novel psychoactive benzofurans, British Journal of Pharmacology, Jul. 2015, pp. 3412-3425.
Rothman, et al., Amphetamine-type central nervous system stimulants release norepinephrine more potently than they release dopamine and serotonin, Synapse, Jan. 1, 2001, pp. 32-41.
Rudnick, et al., The molecular mechanism of "ecstasy" [3, 4-methylenedioxy-methamphetamine (MDMA)]: serotonin transporters are targets for MDMA-induced serotonin release, Proceedings of the National Academy of Sciences, Mar. 1, 1992, pp. 1817-1821.
Schwaninger, et al., Development and validation of LC-HRMS and GC-NICI-MS methods for stereoselective determination of MDMA and its phase I and II metabolites in human urine, Journal of Mass Spectrometry, Jul. 2011, pp. 603-614.
Schwaninger, et al., Stereoselective urinary MDMA (ecstasy) and metabolites excretion kinetics following controlled MDMA administration to humans, Biochemical pharmacology, Jan. 1, 2012, pp. 131-138.
Setola, et al., 3, 4-methylenedioxymethamphetamine (MDMA, "Ecstasy") induces fenfluramine-like proliferative actions on human cardiac valvular interstitial cells in vitro, Molecular Pharmacology, Jun. 1, 2003, pp. 1223-1229.
Steele, et al., Stereochemical effects of 3, 4-methylenedioxymethamphetamine (MDMA) and related amphetamine derivatives on inhibition of uptake of [3H] monoamines into synaptosomes from different regions of rat brain, Biochemical Pharmacology, Jul. 15, 1987, pp. 2297-2303.
Strajhar, et al., Effects of lisdexamfetamine on plasma steroid concentrations compared with d-amphetamine in healthy subjects: A randomized, double-blind, placebo-controlled study, The Journal of steroid biochemistry and molecular biology, Feb. 2019, pp. 212-225.
Sun, et al., Facile and universal immobilization of L-lysine inspired by mussels, J. Mater. Chem., 2012, Journal of Materials Chemistry, 2012, pp. 10035-10041.
Thomas, et al., Characterization of 3, 4-methylenedioxypyrovalerone discrimination in female Sprague-Dawley rats, Behavioural Pharmacology, Jul. 2021, pp. 524-532.
Thomsen, et al., In Vitro Drug Metabolism by Human Carboxylesterase 1: Focus on Angiotensin-Converting Enzyme Inhibitors, Drug Metabolism and Disposition, Jan. 2014, pp. 126-133.
Tournier, et al., Interaction of drugs of abuse and maintenance treatments with human P-glycoprotein (ABCB1) and breast cancer resistance protein (ABCG2), International Journal of Neuropsychopharmacology, Aug. 1, 2010, pp. 905-915.
United States Patent and Trademark Office, International Search Report and Written Opinion for International Application No. PCT/US2022/045587 dated Feb. 1, 2023, 25 pages.
United States Patent and Trademark Office, International Search Report and Written Opinion for International Application No. PCT/US2022/077432 dated Dec. 15, 2022, 14 pages.
Verrico, et al., MDMA (Ecstasy) and human dopamine, norepinephrine, and serotonin transporters: implications for MDMA-induced neurotoxicity and treatment, Psychopharmacology, Jan. 2007, pp. 489-503.
Verweij, A., Impurities in illicit drug preparations; 3,4-methylenedioxyamphetamine and 3-4-methylenedioxymethylamphetamine, Forensic. Sci. Rev., 1992, pp. 1-6.
Weinstock, et al., Ecstasy pill testing: harm minimization gone too far?, Addiction, 2001, pp. 1139-1148.
Weinstock, et al., Synthesis and renal vasodilator activity of some dopamine agonist 1-aryl-2,3,4,5-tetrahydro-1H-3-benzazepine-7,8-diols: halogen and methyl analogs of fenoldopam, Journal of Medicinal Chemistry, 1986, pp. 2315-2325.
Wu, et al., Estimation of tamoxifen metabolite concentrations in the blood of breast cancer patients through CYP2D6 genotype activity score, Breast Cancer Research and Treatment, 2012, pp. 677-683.
Young, et al., MDMA (N-methyl-3,4-methylenedioxyamphetamine) and its Stereoisomers: Similarities and Differences in Behavioral Effects in an Automated Activity Apparatus in Mice, Pharmacol Biochem Behav., Jan. 2008, pp. 318-331.

* cited by examiner

NITRIC OXIDE RELEASING PRODRUGS OF MDA AND MDMA

CROSS-REFERENCE TO RELATED APPLICATION

The present application claims the benefit of priority to U.S. Provisional Application No. 63/294,225, filed Dec. 28, 2021, the contents of which are hereby incorporated by reference in its entirety.

BRIEF SUMMARY OF THE INVENTION

The present disclosure provides MDA or MDMA derivatives that release nitric oxide in vivo.

The present disclosure provides prodrugs of MDMA, MDA, and derivatives thereof, as well as pharmaceutical compositions thereof.

In embodiments, the present disclosure provides a compound of Formula (I):

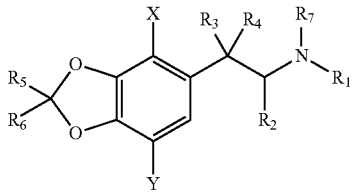

or a pharmaceutically acceptable salt thereof; wherein,
$R_1$ is —(C=O)($CR_9R_{9'}$)$_n$—$ONO_2$ or —(C=O)($CR_9R_{9'}$)$_m$—CH($NH_2$)$CH_2ONO_2$;
$R_2$ is H, $C_1$-$C_4$ alkyl, or $CF_3$;
$R_3$ and $R_4$ are independently H or F;
$R_5$ and $R_6$ are independently H, $C_1$-$C_6$ alkyl, or $CF_3$;
$R_7$ is H or $CH_3$;
$R_8$ is H, $C_1$-$C_6$ alkyl, or $CF_3$;
$R_9$ and $R_{9'}$ are independently H, halogen, or $C_1$-$C_6$ alkyl;
X and Y are independently H, F, Cl, Br, or $OR^8$;
n is an integer from 1 to 9; and
m is an integer from 1 to 9.

In embodiments, the present disclosure provides a compound selected from Table 1 or a pharmaceutically acceptable salt thereof.

TABLE 1

| Compounds | |
|---|---|
| No. | Structure |
| 1-1 | |
| 1-2 | |
| 1-3 | |
| 1-5 | |
| 1-6 | |
| 1-7 | |

In embodiments, the present disclosure provides a compound of Formula (II):

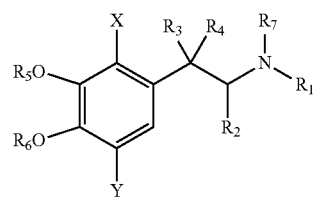

or a pharmaceutically acceptable salt thereof; wherein,
$R_1$ is —(C=O)($CR_9R_{9'}$)$_n$—$ONO_2$ or —(C=O)($CR_9R_{9'}$)$_m$—CH($NH_2$)$CH_2ONO_2$;
$R_2$ is H, $C_1$-$C_4$ alkyl or $CF_3$;
$R_3$ and $R_4$ are independently H or F;
$R_5$ and $R_6$ are independently H, $C_1$-$C_6$ alkyl, or $CF_3$;
$R_7$ is H or $CH_3$;
$R_8$ is H, $C_1$-$C_6$ alkyl, or CF;
$R_9$ and $R_{9'}$ are independently H, halogen, or $C_1$-$C_6$ alkyl;
X and Y are independently H, F, Cl, Br, or $OR^8$,
n is an integer from 1 to 9; and
m is an integer from 1 to 9.

In embodiments, the present disclosure provides a compound of Formula (III):

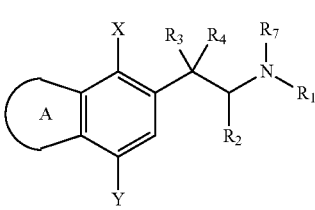

or a pharmaceutically acceptable salt thereof; wherein,
A is

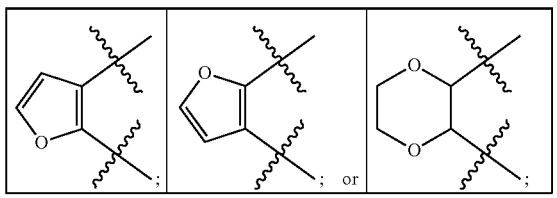 [SMILES: *c1ccoc1* ; *c1ccoc1* ; *C1OCCOC1*]

$R_1$ is —(C=O)($CR_9R_{9'}$)$_n$—$ONO_2$ or —(C=O)($CR_9R_{9'}$)$_m$—CH($NH_2$)$CH_2ONO_2$,
$R_2$ is H, $C_1$-$C_4$ alkyl or $CF_3$;
$R_3$ and $R_4$ are independently H or F;
$R_7$ is H or $CH_3$;
$R_8$ is H, $C_1$-$C_6$ alkyl, or $CF_3$;
X and Y are independently H, F, Cl, Br, or $OR^8$;
n is an integer from 1 to 9; and
m is an integer from 1 to 9.

In embodiments, the present disclosure provides a compound selected from Table 2 or a pharmaceutically acceptable salt thereof.

TABLE 2

Compounds

| No. | Structure |
|---|---|
| 2-1 | 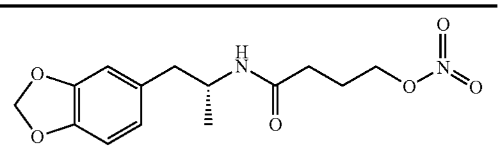 |
| 2-2 | 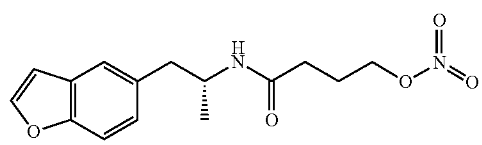 [SMILES: C[C@H](Cc1ccc2occc2c1)NC(=O)CCCO[N+](=O)[O-]] |
| 2-3 | 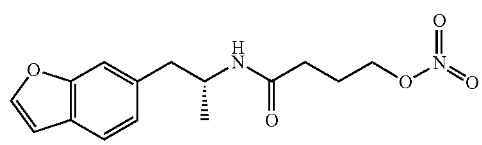 [SMILES: C[C@H](Cc1ccc2ccoc2c1)NC(=O)CCCO[N+](=O)[O-]] |
| 2-4 | 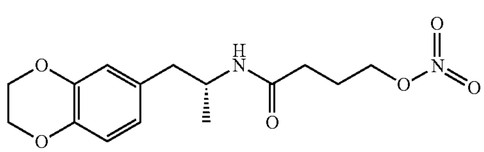 [SMILES: C[C@H](Cc1ccc2c(c1)OCCO2)NC(=O)CCCO[N+](=O)[O-]] |
| 2-5 | 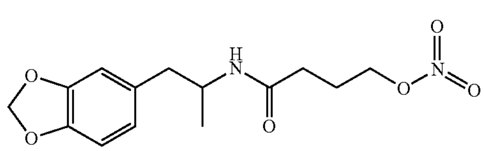 [SMILES: CC(Cc1ccc2c(c1)OCO2)NC(=O)CCCO[N+](=O)[O-]] |
| 2-6 | 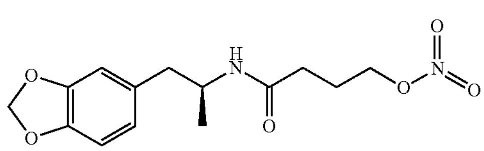 [SMILES: C[C@@H](Cc1ccc2c(c1)OCO2)NC(=O)CCCO[N+](=O)[O-]] |

TABLE 2-continued

Compounds

| No. | Structure |
|---|---|
| 2-7 | 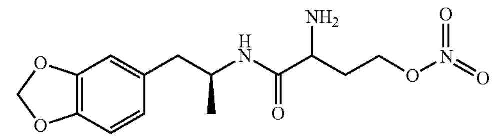 [SMILES: C[C@@H](Cc1ccc2c(c1)OCO2)NC(=O)C(N)CCO[N+](=O)[O-]] |
| 2-8 | 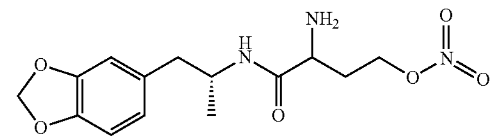 [SMILES: C[C@H](Cc1ccc2c(c1)OCO2)NC(=O)C(N)CCO[N+](=O)[O-]] |
| 2-9 | 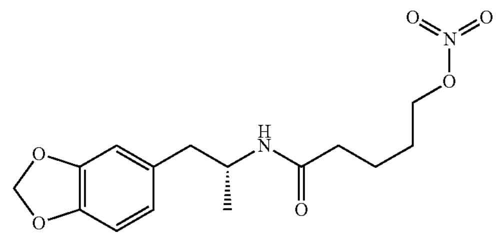 [SMILES: C[C@H](Cc1ccc2c(c1)OCO2)NC(=O)CCCCO[N+](=O)[O-]] |
| 2-10 | 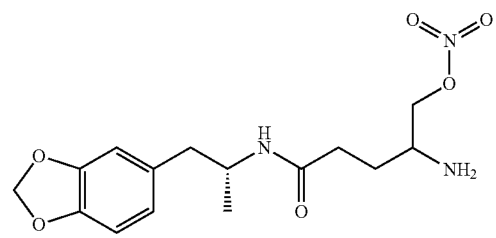 [SMILES: C[C@H](Cc1ccc2c(c1)OCO2)NC(=O)CCC(N)CO[N+](=O)[O-]] |

In some embodiments, present disclosure provides a pharmaceutical composition comprising a therapeutically effective amount of one or more compounds of the present disclosure (e.g., a compound of Formula (I), (II), (III), Table 1 or Table 2) or a pharmaceutically acceptable salt thereof and a pharmaceutically acceptable excipient.

DETAILED DESCRIPTION OF THE INVENTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "administer," "administering" or "administration" as used herein refer to administering a compound or pharmaceutically acceptable salt of the compound or a composition or formulation comprising the compound or pharmaceutically acceptable salt of the compound to a patient.

The term "treating" as used herein with regard to a patient or subject, refers to improving at least one symptom of the patient's or subject's disorder. In some embodiments, treating can be improving, or at least partially ameliorating a disorder or one or more symptoms of a disorder.

The term "therapeutically effective" applied to dose or amount refers to that quantity of a compound or pharmaceutical formulation that is sufficient to result in a desired clinical benefit after administration to a patient or subject in need thereof.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, sec-propyl, n-butyl, sec-butyl, t-butyl, n-pentyl, n-hexyl, n-heptyl, n-octyl, n-nonyl, n-decyl, n-undecyl, and n-dodecyl. Unless stated otherwise specifically in the specification, an alkyl group can be optionally substituted.

"Alkoxy" refers to a group of the formula —ORa where Ra is an alkyl, alkenyl or alknyl as defined above containing one to twelve carbon atoms. Unless stated otherwise specifically in the specification, an alkoxy group can be optionally substituted.

"Haloalkyl" refers to an alkyl, as defined above, that is substituted by one or more halo radicals, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

The term "substituted" used herein means any of the groups described herein (e.g., alkyl, alkenyl, alkynyl, alkoxy, aryl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

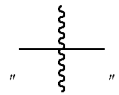

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

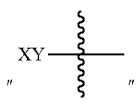

indicates that the chemical entity "XY" is bonded to another chemical entity via the point of attachment bond. Furthermore, the specific point of attachment to the non-depicted chemical entity can be specified by inference. For example, the compound $CH_3$-$R^{3X}$, wherein $R^{3X}$ is H or

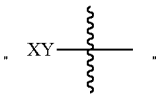

infers that when $R^{3X}$ is "XY", the point of attachment bond is the same bond as the bond by which $R^{3X}$ is depicted as being bonded to $CH_3$.

Compounds

In one aspect, the present disclosure provides prodrugs of MDMA, MDA, and derivatives thereof, that release nitric oxide in vivo.

In embodiments, the present disclosure provides a compound of Formula (I):

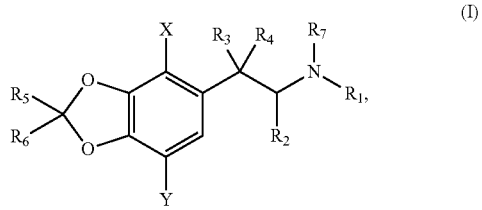

or a pharmaceutically acceptable salt thereof; wherein,
$R_1$ is —(C=O)($CR_9R_{9'}$)$_n$—$ONO_2$ or —(C=O)($CR_9R_{9'}$)$_m$—CH($NH_2$)$CH_2ONO_2$;
$R_2$ is H, $C_1$-$C_4$ alkyl, or $CF_3$;
$R_3$ and $R_4$ are independently H or F;
$R_4$ and $R_6$ are independently H, $C_1$-$C_6$ alkyl, or $CF_3$;
$R_7$ is H or $CH_3$; and
$R_8$ is H, $C_1$-$C_6$ alkyl, or $CF_3$;
$R_9$ and $R_9'$ are independently H, halogen, or $C_1$-$C_6$ alkyl;
X and Y are independently H, F, Cl, Br, or $OR^8$;

n is an integer from 1 to 9; and
m is an integer from 1 to 9.

In embodiments of the compounds of Formula (I), $R_1$ is —(C=O)($CH_2$)$_n$—$ONO_2$.

In embodiments of the compounds of Formula (I), $R_1$ is —(C=O)($CH_2$)$_m$—CH($NH_2$)$CH_2ONO_2$.

In embodiments of the compounds of Formula (I), $R_2$ is $C_1$-$C_4$ alkyl.

In embodiments of the compounds of Formula (I), $R_2$ is methyl.

In embodiments of the compounds of Formula (I), $R_2$ is $CF_3$.

In embodiments of the compounds of Formula (I), $R_3$ and $R_4$ are H.

In embodiments of the compounds of Formula (I), $R_3$ and $R_4$ are F.

In embodiments of the compounds of Formula (I), $R_5$ and $R_6$ are H.

In embodiments of the compounds of Formula (I), $R_5$ and $R_6$ are $C_1$-$C_6$ alkyl.

In embodiments of the compounds of Formula (I), $R_5$ and $R_6$ are $CF_3$.

In embodiments of the compounds of Formula (I), $R_7$ is H.

In embodiments of the compounds of Formula (I), $R_7$ is $CH_3$.

In embodiments of the compounds of Formula (I), X and Y are H.

In embodiments of the compounds of Formula (I), X and Y are F.

In embodiments of the compounds of Formula (I), m is 2.

In embodiments of the compounds of Formula (I), n is 3.

In embodiments of the compounds of Formula (I), n is 4.

In embodiments, the present disclosure provides a compound selected from Table 1 or a pharmaceutically acceptable salt thereof.

TABLE 1

| No. | Compounds Structure |
|---|---|
| 1-1 | ![structure] |
| 1-2 | ![structure] |
| 1-3 | ![structure] |
| 1-5 | ![structure] |

TABLE 1-continued

Compounds

| No. | Structure |
|---|---|
| 1-6 | 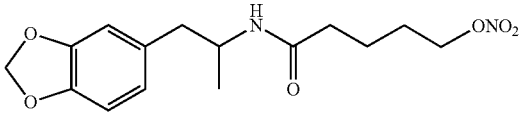 |
| 1-7 | 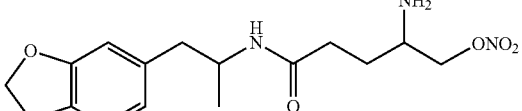 |

In embodiments, the present disclosure provides a compound of Formula (II):

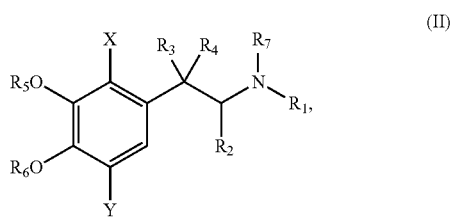

(II)

or a pharmaceutically acceptable salt thereof; wherein,
$R_1$ is —(C=O)(CR$_9$R$_{9'}$)$_n$—ONO$_2$ or —(C=O)(CR$_9$R$_{9'}$)$_m$—CH(NH$_2$)CH$_2$ONO$_2$;
$R_2$ is H, $C_1$-$C_4$ alkyl, or CF$_3$;
$R_3$ and $R_4$ are independently H or F;
$R_5$ and $R_6$ are independently H, $C_1$-$C_6$ alkyl, or CF$_3$;
$R_7$ is H or CH$_3$;
$R_8$ is H, $C_1$-$C_6$ alkyl, or CF$_3$;
$R_9$ and $R_{9'}$ are independently H, halogen, or $C_1$-$C_6$ alkyl;
X and Y are independently H, F, Cl, Br, or OR$^8$;
n is an integer from 1 to 9; and
m is an integer from 1 to 9.

In embodiments, the present disclosure provides a compound of Formula (III):

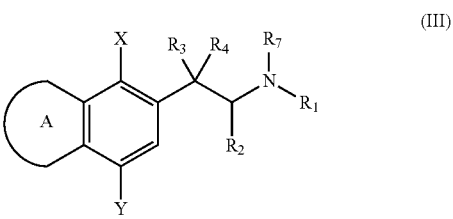

(III)

or a pharmaceutically acceptable salt thereof; wherein,
A is

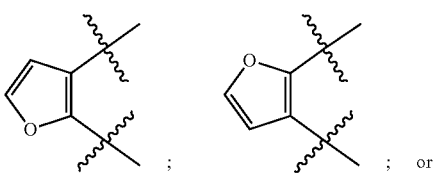

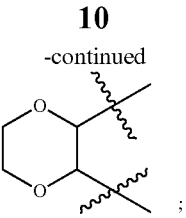

;

$R_1$ is —(C=O)(CR$_9$R$_{9'}$)$_n$—ONO$_2$ or —(C=O)(CR$_9$R$_{9'}$)$_m$—CH(NH$_2$)CH$_2$ONO$_2$;
$R_2$ is H, $C_1$-$C_4$ alkyl or CF$_3$;
$R_3$ and $R_4$ are independently H or F;
$R_5$ and $R_6$ are independently H, $C_1$-$C_6$ alkyl, or CF$_3$;
$R_7$ is H or CH$_3$;
$R_8$ is H, $C_1$-$C_6$ alkyl, or CF$_3$;
$R_9$ and $R_{9'}$ are independently H, halogen, or $C_1$-$C_6$ alkyl;
X and Y are independently H, F, Cl, Br, or OR$^8$;
n is an integer from 1 to 9; and
m is an integer from 1 to 9.

In embodiments of the compounds of Formula (III), A is

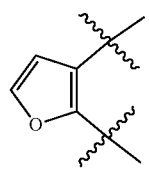

.

In embodiments of the compounds of Formula (III), A is

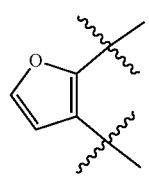

.

In embodiments of the compounds of Formula (III), A is

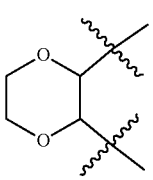

.

In embodiments of the compounds of Formula (II) or Formula (III), $R_1$ is —(C=O)(CR$_9$R$_{9'}$)$_n$—ONO$_2$.

In embodiments of the compounds of Formula (II) or Formula (III), $R_1$ is —(C=O)(CR$_9$R$_{9'}$)$_m$—CH(NH$_2$)CH$_2$ONO$_2$.

In embodiments of the compounds of Formula (II) or Formula (III), $R_9$ and $R_{9'}$ are independently halogen or $C_1$-$C_6$ alkyl.

In embodiments of the compounds of Formula (II) or Formula (III), $R_1$ is —(C=O)(CH$_2$)$_n$—ONO$_2$.

In embodiments of the compounds of Formula (II) or Formula (III), $R_1$ is —(C=O)(CH$_2$)$_m$—CH(NH$_2$)CH$_2$ONO$_2$.

In embodiments of the compounds of Formula (II) or Formula (III), $R_2$ is $C_1$-$C_4$ alkyl.

In embodiments of the compounds of Formula (II) or Formula (III), $R_2$ is methyl.

In embodiments of the compounds of Formula (II) or Formula (III), $R_2$ is $CF_3$.

In embodiments of the compounds of Formula (II) or Formula (III), $R_3$ and $R_4$ are H.

In embodiments of the compounds of Formula (II) or Formula (III), $R_3$ and $R_4$ are F.

In embodiments of the compounds of Formula (II), $R_5$ and $R_6$ are H.

In embodiments of the compounds of Formula (II), $R_5$ and $R_6$ are $C_1$-$C_6$ alkyl.

In embodiments of the compounds of Formula (II), $R_5$ and $R_6$ are $CF_3$.

In embodiments of the compounds of Formula (II) or Formula (III), $R_7$ is H.

In embodiments of the compounds of Formula (II) or Formula (III), $R_7$ is $CH_3$.

In embodiments of the compounds of Formula (II) or Formula (III), X and Y are H.

In embodiments of the compounds of Formula (II) or Formula (III), X and Y are F.

In embodiments of the compounds of Formula (II) or Formula (III), m is 2.

In embodiments of the compounds of Formula (II) or Formula (III), n is 3.

In embodiments of the compounds of Formula (II) or Formula (III), n is 4.

In embodiments, the present disclosure provides a compound selected from Table 2 or a pharmaceutically acceptable salt thereof.

TABLE 2

| No. | Structure | Name |
|---|---|---|
| 2-1 | 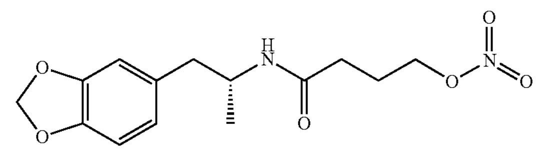 [SMILES: C[C@H](Cc1ccc2c(c1)OCO2)NC(=O)CCCO[N+](=O)[O-]] | (R)-4-((1-(benzo[d][1,3]dioxol-5-yl)propan-2-yl)amino)-4-oxobutyl nitrate |
| 2-2 | 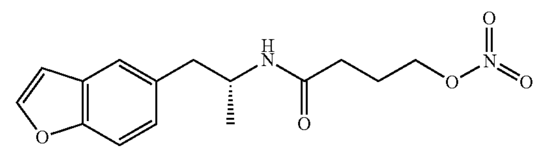 [SMILES: C[C@H](Cc1ccc2occc2c1)NC(=O)CCCO[N+](=O)[O-]] | (R)-4-((1-(benzofuran-5-yl)propan-2-yl)amino)-4-oxobutyl nitrate |
| 2-3 | 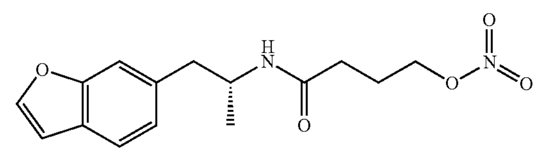 [SMILES: C[C@H](Cc1ccc2ccoc2c1)NC(=O)CCCO[N+](=O)[O-]] | (R)-4-((1-(benzofuran-6-yl)propan-2-yl)amino)-4-oxobutyl nitrate |
| 2-4 | 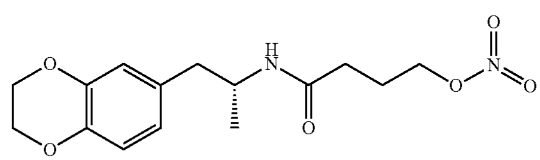 [SMILES: C[C@H](Cc1ccc2c(c1)OCCO2)NC(=O)CCCO[N+](=O)[O-]] | (R)-4-((1-(2,3-dihydrobenzo[b][1,4]dioxin-6-yl)propan-2-yl)amino)-4-oxobutyl nitrate |
| 2-5 | 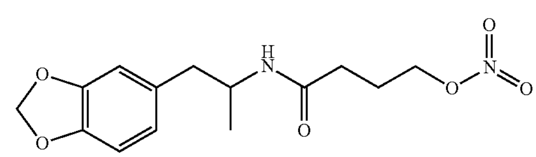 [SMILES: CC(Cc1ccc2c(c1)OCO2)NC(=O)CCCO[N+](=O)[O-]] | 4-((1-(benzo[d][1,3]dioxol-5-yl)propan-2-yl)amino)-4-oxobutyl nitrate |
| 2-6 | 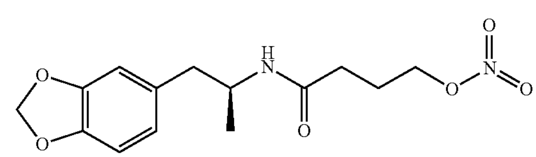 [SMILES: C[C@@H](Cc1ccc2c(c1)OCO2)NC(=O)CCCO[N+](=O)[O-]] | (S)-4-((1-(benzo[d][1,3]dioxol-5-yl)propan-2-yl)amino)-4-oxobutyl nitrate |
| 2-7 | 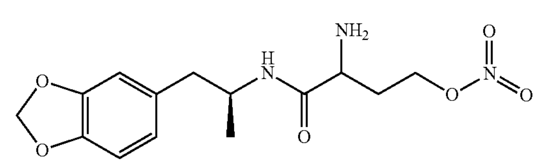 [SMILES: C[C@@H](Cc1ccc2c(c1)OCO2)NC(=O)C(N)CCO[N+](=O)[O-]] | 3-amino-4-(((S)-1-(benzo[d][1,3]dioxol-5-yl)propan-2-yl)amino)-4-oxobutyl nitrate |

TABLE 2-continued

Compounds

| No. | Structure | Name |
|---|---|---|
| 2-8 | 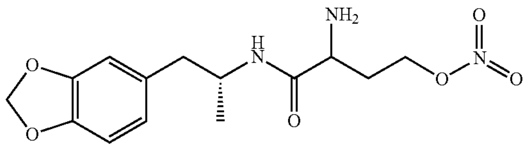 [SMILES: C[C@H](Cc1ccc2c(c1)OCO2)NC(=O)C(N)CCO[N+](=O)[O-]] | 3-amino-4-(((R)-1-(benzo[d][1,3]dioxol-5-yl)propan-2-yl)amino)-4-oxobutyl nitrate |
| 2-9 | 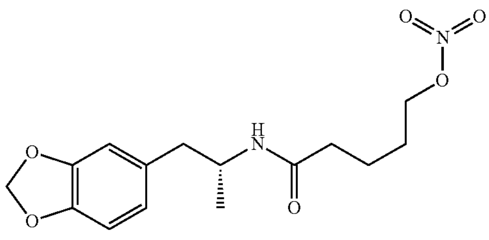 [SMILES: C[C@H](Cc1ccc2c(c1)OCO2)NC(=O)CCCCO[N+](=O)[O-]] | (R)-5-((1-(benzo[d][1,3]dioxol-5-yl)propan-2-yl)amino)-5-oxopentyl nitrate |
| 2-10 | 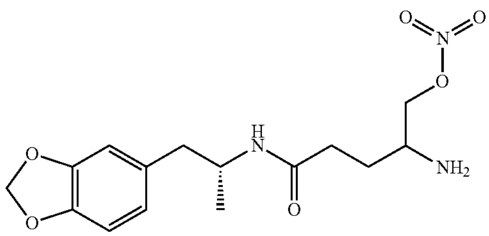 [SMILES: C[C@H](Cc1ccc2c(c1)OCO2)NC(=O)CCC(N)CO[N+](=O)[O-]] | 2-amino-5-(((R)-1-(benzo[d][1,3]dioxol-5-yl)propan-2-yl)amino)-5-oxopentyl nitrate |

Compositions

In one aspect, the present disclosure provides a pharmaceutical composition comprising a therapeutically effective amount of one or more compounds of the present disclosure (e.g., a compound of Formula (I), (II), (III), Table 1 or Table 2) or a pharmaceutically acceptable salt thereof and a pharmaceutically acceptable excipient.

The pharmaceutically acceptable excipients and adjuvants are added to the composition or formulation for a variety of purposes. In some embodiments, a pharmaceutical composition comprising one or more compounds disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Methods of Treatment

In embodiments, the present disclosure provides a method of treating or preventing neurological disorders in a subject in need thereof, the method comprising administering to the subject a therapeutically effective amount of a compound disclosed herein, e.g., Formula (I), (II), (III), Table 1 or Table 2, or a pharmaceutically acceptable salt thereof.

In embodiments, the neurological disorder is a mood disorder. In embodiments, the mood disorder is clinical depression, postnatal depression or postpartum depression, perinatal depression, atypical depression, melancholic depression, psychotic major depression, cationic depression, seasonal affective disorder, dysthymia, double depression, depressive personality disorder, recurrent brief depression, major depressive disorder, minor depressive disorder, bipolar disorder or manic depressive disorder, depression caused by chronic medical conditions, treatment-resistant depression, refractory depression, suicidality, suicidal ideation, or suicidal behavior. In embodiments, the method described herein provides therapeutic effect to a subject suffering from depression (e.g., moderate or severe depression). In some embodiments, the mood disorder is associated with neuroendocrine diseases and disorders, neurodegenerative diseases and disorders (e.g., epilepsy), movement disorders, tremor (e.g., Parkinson's Disease), or women's health disorders or conditions. In embodiments the mood disorder is depression. In embodiments, the mood disorder is treatment-resistant depression or major depressive disorder. In some embodiments, the mood disorder is major depressive disorder. In embodiments, the mood disorder is treatment-resistant depression.

In some embodiments, the present disclosure provides a method of treating or preventing PTSD, mood disorders, general anxiety disorder, addictive disorders, and/or drug dependence in a subject in need thereof, the method comprising administering to the subject a therapeutically effective amount of a compound disclosed herein, e.g., a compound of Formula (I), (II), (III), Table 1, or Table 2, a pharmaceutically acceptable salt thereof, or a pharmaceutical composition thereof.

In embodiments, the compounds of the present disclosure are used to treat PTSD. In embodiments, the compounds of the present disclosure are used for induction and maintenance therapy to treat PTSD. In embodiments, the compounds of the present disclosure are used to treat PTSD with an improved safety profile when compared to treatment with the entactogenic, oneirophrenic or psychedelic compound (e.g. MDMA or related compound, psilocybin or dimethyltryptamine) alone. In embodiments, the compounds of the present disclosure are used for induction and maintenance therapy to treat PTSD with an improved safety profile when compared to treatment with the entactogenic, oneirophrenic or psychedelic compound (e.g. MDMA or related compound, psilocybin or dimethyltryptamine) alone.

In embodiments, the compounds of the present disclosure are used to treat behavioral or mood disorders. Examples of behavioral or mood disorders include anxiety, such as social anxiety in autistic subjects (e.g. autistic adults) and anxiety related to life-threatening illnesses, stress (where moderation thereof is measured, for example, by effects on amygdala responses). In some embodiments, the anxiety disorder is panic disorder, obsessive-compulsive disorder, or general anxiety disorder. Other examples include lack of motivation, attention, accuracy, speed of response, perseveration, and/or cognitive engagement. Further examples include depression (e.g., MDD or TRD), attention disorders, disorders of executive function and/or cognitive engagement, obsessive compulsive disorder, bipolar disorder, panic disorder, phobia, schizophrenia, psychopathy, antisocial personality disorder and/or neurocognitive disorders.

In embodiments, the compounds the present disclosure are used to treat an addictive disorder. In embodiments, the addictive disorder is alcohol abuse, substance abuse, smoking, or obesity. In embodiments, the disorder is an eating disorder (anorexia nervosa, bulimia, nervosa, binge eating disorder, etc.) or an auditory disorder.

In embodiments, the disorder is an impulsive disorder. In embodiments, the impulsive disorder is attention deficit hyperactivity disorder (ADHD), attention deficit disorder (ADD), Tourette's syndrome or autism.

In embodiments, the disorder is a compulsive disorder. In embodiments, the compulsive disorder is obsessive compulsive disorder (OCD), gambling, or aberrant sexual behavior.

In embodiments, the disorder is a personality disorder. In embodiments, the personality disorder is conduct disorder, antisocial personality, or aggressive behavior.

NUMBERED EMBODIMENTS

In addition to the disclosure above, the Examples below, and the appended claims, the disclosure sets for the following numbered embodiments.
1. A of Formula (I):

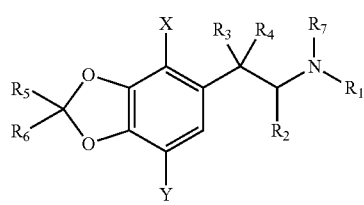

or a pharmaceutically acceptable salt thereof; wherein,
$R_1$ is —(C=O)(CR$_9$R$_{9'}$)$_n$—ONO$_2$ or —(C=O)(CR$_9$R$_{9'}$)$_m$—CH(NH$_2$)CH$_2$ONO$_2$;
$R_2$ is H, $C_1$-$C_4$ alkyl, or CF$_3$;
$R_3$ and $R_4$ are independently H or F;
$R_5$ and $R_6$ are independently H, $C_1$-$C_6$ alkyl, or CF$_3$;
$R_7$ is H or CH$_3$;
$R_8$ is H, $C_1$-$C_6$ alkyl, or CF$_3$;
$R_9$ and $R_{9'}$ are independently H, halogen, or $C_1$-$C_6$ alkyl;
X and Y are independently H, F, Cl, Br, or OR$^8$,
n is an integer from 1 to 9; and
is an integer from 1 to 9.
2. The compound of embodiment 1, wherein $R_1$ is —(C=O)(CR$_9$R$_{9'}$)$_n$—ONO$_2$.
3. The compound of embodiment 1, wherein $R_1$ is —(C=O)(CR$_9$R$_{9'}$)$_m$—CH(NH$_2$)CH$_2$ONO$_2$.
3a. The compound of embodiment 1, wherein $R_1$ is —(C=O)(CH$_2$)$_n$—ONO$_2$.
4. The compound of embodiment 1, wherein $R_1$ is —(C=O)(CH$_2$)$_m$—CH(NH$_2$)CH$_2$ONO$_2$.
5. The compound of any one of embodiments 1-4, wherein $R_2$ is $C_1$-$C_4$ alkyl.
6. The compound of any one of embodiments 1-4, wherein $R_2$ is methyl.
7 The compound of any one of embodiments 1-4, wherein $R_2$ is CF$_3$.
8. The compound of any one of embodiments 1-7, wherein $R_3$ and $R_4$ are H.
9. The compound of any one of embodiments 1-7, wherein $R_3$ and $R_4$ are F.
10. The compound of any one of embodiments 1-9, wherein $R_5$ and $R_6$ are H.
11. The compound of any one of embodiments 1-9, wherein $R_5$ and $R_6$ are $C_1$-$C_6$ alkyl.
12. The compound of any one of embodiments 1-9, wherein $R_5$ and $R_6$ are CF$_3$.
13. The compound of any one of embodiments 1-12, wherein $R_7$ is H.
14. The compound of any one of embodiments 1-12, wherein $R_7$ is CH$_3$.
15. The compound of any one of embodiments 1-14, wherein X and Y are H.
16. The compound of any one of embodiments 1-14, wherein X and Y are F.
17. The compound of any one of embodiments 1-16, wherein m is 2.
18. The compound of any one of embodiments 1-17, wherein n is 3.
19. The compound of any one of embodiments 1-17, wherein n is 4.
20. The compound of embodiment 1, having the formula:

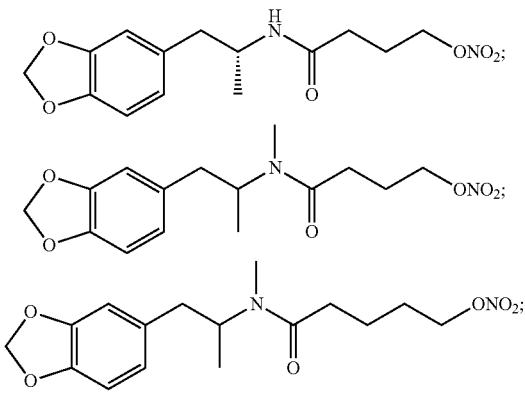

-continued

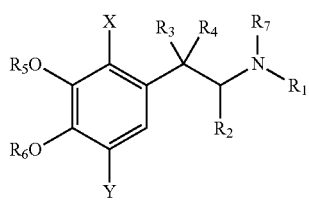

or a pharmaceutically acceptable salt thereof.

21. A compound of Formula (II):

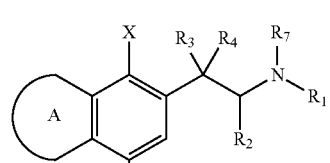

or a pharmaceutically acceptable salt thereof; wherein,
$R_1$ is —(C=O)(CR$_9$R$_{9'}$)$_n$—ONO$_2$ or —(C=O)(CR$_9$R$_{9'}$)$_m$—CH(NH$_2$)CH$_2$ONO$_2$;
$R_2$ is H, $C_1$-$C_4$ alkyl or CF$_3$;
$R_3$ and $R_4$ are independently H or F;
$R_5$ and $R_6$ are independently H, $C_1$-$C_6$ alkyl, or CF$_3$;
$R_7$ is H or CH$_3$;
$R_8$ is H, $C_1$-$C_6$ alkyl, or CF;
$R_9$ and $R_{9'}$ are independently H, halogen, or $C_1$-$C_6$ alkyl;
X and Y are independently H, F, Cl, Br, or OR$^8$;
n is an integer from 1 to 9; and
m is an integer from 1 to 9.

22. The compound of embodiment 21, wherein $R_1$ is —(C=O)(CR$_9$R$_{9'}$)$_n$—ONO$_2$.

23. The compound of embodiment 21, wherein $R_1$ is —(C=O)(CR$_9$R$_{9'}$)$_m$—CH(NH$_2$)CH$_2$ONO$_2$.

24. The compound of embodiment 21, wherein $R_1$ is —(C=O)(CH$_2$)$_n$—ONO$_2$.

25. The compound of embodiment 21, wherein $R_1$ is —(C=O)(CH$_2$)$_m$—CH(NH$_2$)CH$_2$ONO$_2$.

26. The compound of any one of embodiments 21-25, wherein $R_2$ is $C_1$-$C_4$ alkyl.

27. The compound of any one of embodiments 21-26, wherein $R_2$ is methyl.

28. The compound of any one of embodiments 21-25, wherein $R_2$ is CF$_3$.

29. The compound of any one of embodiments 21-28, wherein $R_3$ and $R_4$ are H.

30. The compound of any one of embodiments 21-28, wherein $R_3$ and $R_4$ are F.

31. The compound of any one of embodiments 21-30, wherein $R_5$ and $R_6$ are H.

32. The compound of any one of embodiments 21-30, wherein $R_5$ and $R_6$ are $C_1$-$C_6$ alkyl.

33. The compound of any one of embodiments 21-30, wherein $R_5$ and $R_6$ are CF$_3$.

34. The compound of any one of embodiments 21-33, wherein $R_7$ is H.

35. The compound of any one of embodiments 21-33, wherein $R_7$ is CH$_3$.

36. The compound of any one of embodiments 21-35, wherein X and Y are H.

37. The compound of any one of embodiments 21-35, wherein X and Y are F.

38. The compound of any one of embodiments 21-37, wherein m is 2.

39. The compound of any one of embodiments 21-38, wherein n is 3.

40. The compound of any one of embodiments 21-38, wherein n is 4.

41. A compound of Formula (III):

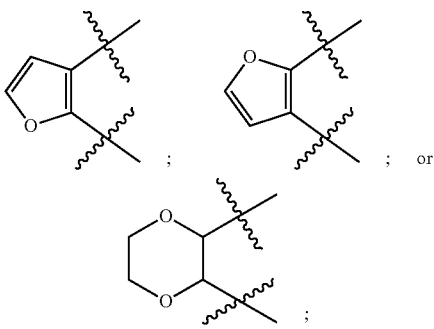

or a pharmaceutically acceptable salt thereof; wherein, A is $R_1$ is —(C=O)(CR$_9$R$_{9'}$)$_n$—ONO$_2$ or —(C=O)(CR$_9$R$_{9'}$)$_m$—CH(NH$_2$)CH$_2$ONO$_2$,
$R_2$ is H, $C_1$-$C_4$ alkyl or CF$_3$;
$R_3$ and $R_4$ are independently H or F;
$R_5$ and $R_6$ are independently H, $C_1$-$C_6$ alkyl, or CF$_3$;
$R_7$ is H or CH$_3$;
$R_8$ is H, $C_1$-$C_6$ alkyl, or CF$_3$;
X and Y are independently H, F, Cl, Br, or OR$^8$;
n is an integer from 1 to 9; and
m is an integer from 1 to 9.

42. The compound of embodiment 41, wherein $R_1$ is —(C=O)(CR$_9$R$_{9'}$)$_n$—ONO$_2$.

43. The compound of embodiment 41, wherein $R_1$ is —(C=O)(CR$_9$R$_{9'}$)$_m$—CH(NH$_2$)CH$_2$ONO$_2$.

44. The compound of embodiment 41, wherein $R_1$ is —(C=O)(CH$_2$)$_n$—ONO$_2$.

45. The compound of embodiment 41, wherein $R_1$ is —(C=O)(CH$_2$)$_m$—CH(NH$_2$)CH$_2$ONO$_2$.

46. The compound of any one of embodiments 41-45, wherein $R_2$ is $C_1$-$C_4$ alkyl.
47. The compound of any one of embodiments 41-46, wherein $R_2$ is methyl.
48. The compound of any one of embodiments 41-45, wherein $R_2$ is $CF_3$.
49. The compound of any one of embodiments 41-48, wherein $R_3$ and $R_4$ are H.
50. The compound of any one of embodiments 41-48, wherein $R_3$ and $R_4$ are F.
51. The compound of any one of embodiments 41-50, wherein $R_7$ is H.
52. The compound of any one of embodiments 41-50, wherein $R_7$ is $CH_3$.
53. The compound of any one of embodiments 41-52, wherein X and Y are H.
54. The compound of any one of embodiments 41-52, wherein X and Y are F.
55. The compound of any one of embodiments 41-54, wherein m is 2.
56. The compound of any one of embodiments 41-55, wherein n is 3.
57. The compound of any one of embodiments 41-55, wherein n is 4.
58. The compound of any one of embodiments 41-57, wherein A is

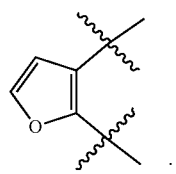 [SMILES: *c1ccoc1*]

59. The compound of any one of embodiments 41-57, wherein A is

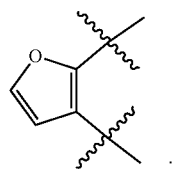 [SMILES: *c1ccoc1*]

60. The compound of any one of embodiments 41-57, wherein A is

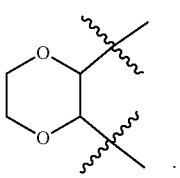 [SMILES: *C1OCCOC1*]

61. A compound having the formula:

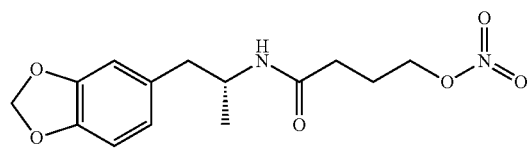

-continued

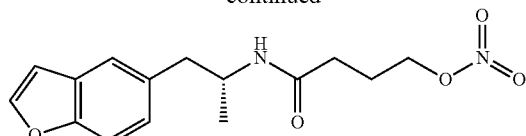

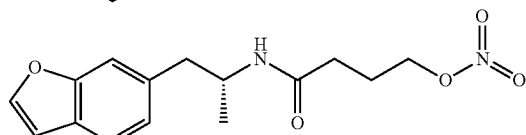

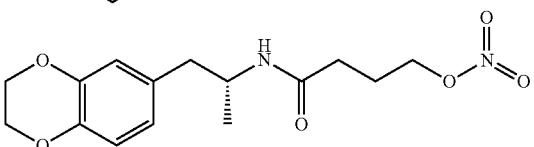

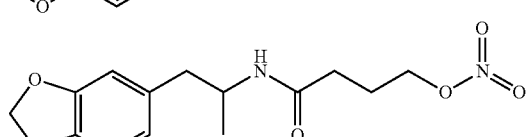

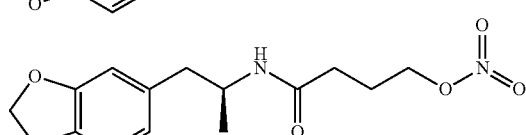

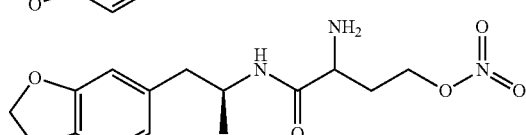

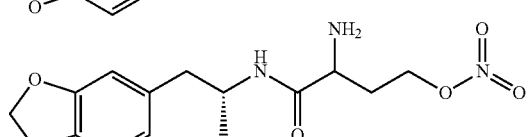

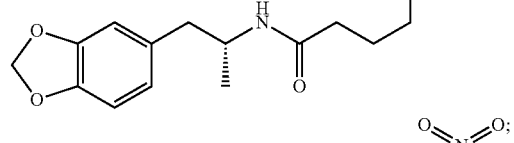

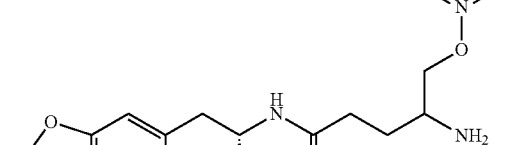

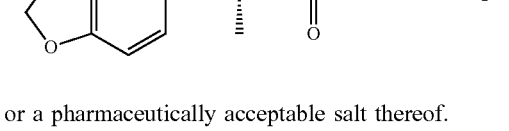

or a pharmaceutically acceptable salt thereof.
62. A pharmaceutical composition, comprising a compound of any one of embodiments 1-61 and a pharmaceutically acceptable excipient.
63. A method of treating a mental health disease or disorder, the method comprising administering a therapeutically effective amount of a compound of any one of embodiments 1-61 or the pharmaceutical composition of embodiment 62.

EXAMPLES

Example 1

Methods of Preparing the Compounds of the Present Disclosure

The following schemes provide methods for preparing the compounds of the present disclosure.

Unless otherwise noted, all materials/reagents were obtained from commercial suppliers and used without further purification. Reactions were monitored by LC-MS and/or thin layer chromatography (TLC) on silica gel 60 F254 (0.2 mm) pre-coated aluminum foil or glass-backed and visualized using UV light. $^1$HNMR (400 MHz) spectra was recorded on Broker spectrometers at RT with TMS or the residual solvent peak as the internal standard. Chemical shifts are given in (δ) and the coupling constants (J) are given as absolute values in Hertz (Hz). The multiplicities in $^1$HNMR spectra are abbreviated as follows: s (singlet), d (doublet), t (triplet), q (quartet), m (multiplet), br or broad (broadened). Preparative HPLC purifications were performed on Shimadzu LC-6AD. All purification work was completed using a Shim-pack PREP-DDS(H)KIT Column. The mobile phases were water (with 0.1% HCO$_2$H) and acetonitrile; all reagents used were of HPLC grade. The flow rate was 10 ml/min. LC-MS analyses were performed on Shimadzu LCMS-2020 equipped with LC-20AD or 30AD pumps, SPD-M20A PDA and Alltech 3300 ELSD; Mobile Phase: A:Water (0.1% Formic acid), B: ACN; 5 minute run; Column: Sepax BR-C18 4.6*50 mm, 3 um; Flow Rate:1.0 ml/min; Oven Temperature: 40° C.; Gradient: 20% B for 0.2 min, increase to70% B within 1.8 min,70% B for 2.8 min, back to 20% B within 0.2 min, 20% B for 2 min). Preparative TLC was performed on Whatman LK6F Silica Gel 60A size 20×20 cm plates with a thickness of 1000 μm or equivalent.

Method A for Preparing Compounds of the Present Disclosure, e.g., Formula 1-1, 1-2,1-3, 1-5, 1-6, 1-7 and 1-8

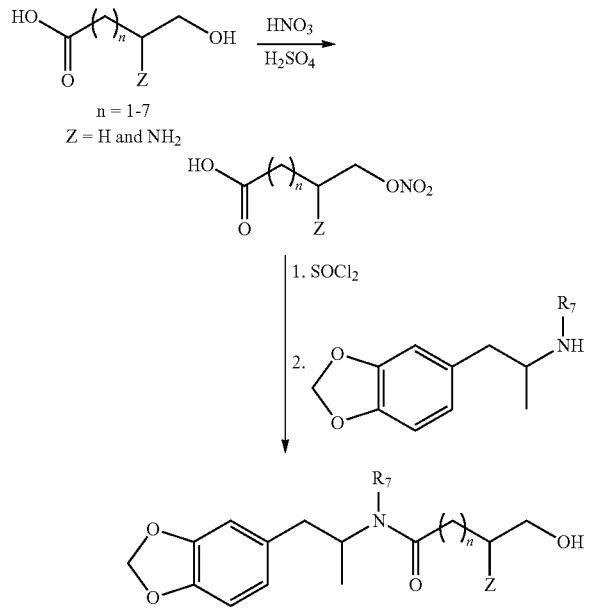

Example 2

Synthesis of 2-1: (R)-4-((1-(benzo[d][1,3]dioxol-5-yl)propan-2-yl)amino) oxobutyl nitrate Intermediate 2-14 was synthesized from commercially avaialbale intermediate 2-1-A (Scheme 1) and was used for the final pro drig synthesis (Scheme 2).

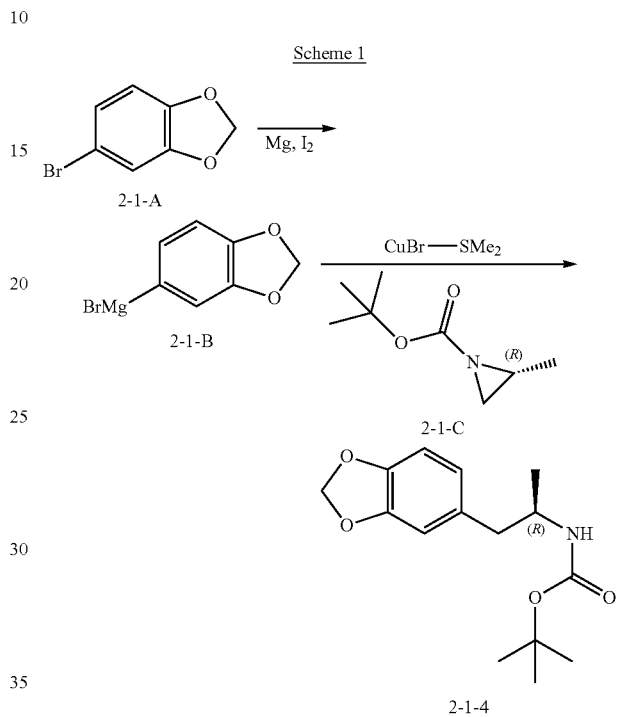

Scheme 1

Synthesis of Intermediate 2-1-B

To a 100 mL flask was charged magnesium (60.4 mg, 2.487 mmol, 2.00 equiv.), iodine (one crystal) and tetrahydrofuran (1.5 mL) at room temperature under nitrogen. 5-Bromo-2H-1,3-benzodioxole, 2-1-A (50 mg) was added to the mixture and heated to 50° C. at which time the iodine color disappeared, and the internal temperature rose to 56° C. 5-Bromo-2H-1,3-benzodioxole (450 mg, total added 500 mg, 2.487 mmol, 2.0 equiv.) was added, via syringe, to the mixture dropwise maintaining an internal temperature of 45-55° over 10 minutes. After addition was complete the syringe was rinsed with THF (0.1 mL) and the rinse charged to the reaction at 49° C. After stirring for 1.5 hours the batch was a clear amber color with an internal temperature of 19.6° C. THF (1 mL) was added. This crude material 2-1-B was used directly for the next steps.

Synthesis of Intermediate 2-1-4

The flask was cooled to 0.8° C. using an ice/water bath then solid CuBrSMe2 (52.3 mg, 0.254 mmol, 0.2 equiv) was charged in one portion. An exotherm to 6° C. was observed. After cooling to 0.5° C. a solution of tert-butyl (2R)-2-methylaziridine-1-carboxylate, 2-1-C (200 mg, 1.272 mmol, 1.0 equiv.) in tetrahydrofuran (0.5 mL) was added over 20 minutes, while maintaining an internal temperature <6° C. After stirring for 4 hours TLC analysis (5:1 heptane/EA) of the brown slurry showed complete reaction. After a further 20 minutes the reaction was quenched with dropwise addition sat. ammonium chloride (5.0 mL), while maintaining an internal temperature <18° C. (3 minutes). After stirring for 12 minutes at room temperature the biphasic mixture was diluted with Ethyl acetate (1.5 mL). The layers were separated, and the aqueous layer was extracted with Ethyl acetate (2×1.5 mL). The combined organic layers dried over sodium sulfate (1.3 g), filtered, and concentrated under reduced pressure. Chromatographic purification in silica, eluting with 0-15% Ethyl acetate/heptane afforded tert-butyl (R)-(1-(benzo[d][1,3]dioxol-5-yl)propan-2-yl)carbamate, 2-1-4 (130 mg, 36% yield) as a white solid. 50 mg purified by reversed Flash with the following conditions: Column: XBridge Prep OBD C18 Column, 30*150 mm, 5 μm; Mobile Phase A: 10 mmol $NH_4HCO_3$+0.05%$NH_3H_2O$, Mobile Phase B: ACN; Flow rate: 60 mL/min; Gradient: 23% B to 53% B in 8 min, 53% B; Wavelength: 254 nm. The fractions of desired product were lyophilized. This resulted in 28.0 mg as a white solid. MS m/z[M−H]⁻ (ESI):278.15. $^1$H NMR (400 MHz, DMSO-$d_6$) δ 6.81-6.61 (m, 4H), 5.95-5.94 (m, 2H), 3.61-3.53 (m, 1H), 2.63-2.58 (m, 1H), 2.49-2.44 (m, 1H), 1.34 (s, 9H), 0.98 (d, J=6.8 Hz, 3H).

Synthesis of Intermediate 2-1: tert-butyl (R)-(1-(benzo[d][1,3]dioxol-5-yl)propan-2-yl)carbamate Synthesis of Intermediate 2-1-2

To a solution of methyl 4-bromobutanoate, 2-1-1 (1 g, 5.56 mmol, 1 equiv.) in dry acetonitrile (20 mL) was added silver nitrate (2.35 g, 13.810 mmol, 2.5 equiv.). The reaction was heated to 80° C. for 4 hours, protected from light. The reaction mixture was filtered through Celite and the solvent removed under reduced pressure. The crude residue suspended in ethyl acetate (20 mL) and filtered through a silica plug. The organic layer was washed with water (10 mL) and brine (10 mL), dried over sodium sulfate, filtered and the solvent removed under reduced pressure to 2-1-2 (800 mg, 89%) as a pale yellow oil, which was used without any further purification.

Synthesis of Intermediate 2-1-3: 4-(nitrooxy)butanoic acid

Methyl 4-(nitrooxy)butanoate 2-1-1 (700 mg, 4.291 mmol, 1 equiv) was dissolved in methanol (16.8 mL) at 5° C. and LiOH (4.2 mL, 2 mol/L in water) was added. The reaction was stirred overnight at 5° C. Solution was acidified to pH 3 with $HC_1$(1 mol/L) and methanol as evaporated. Aqueous phase was extracted with DCM, dried over sodium sulfate and concentrated affording 4-(nitrooxy)butanoic acid, 2-1-3 (350 mg, 55%) as a yellow oil.

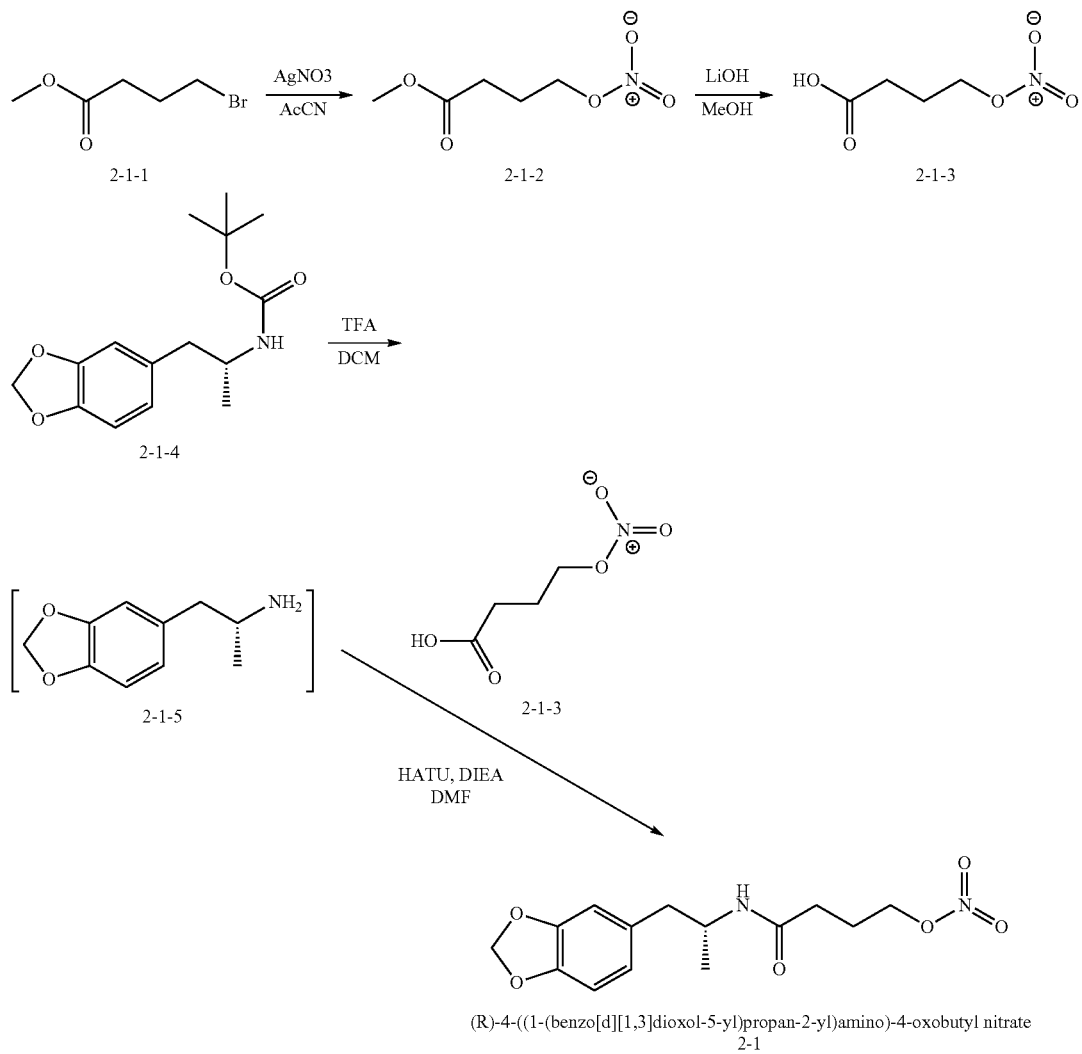

(R)-4-((1-(benzo[d][1,3]dioxol-5-yl)propan-2-yl)amino)-4-oxobutyl nitrate
2-1

Synthesis of Final Product 2-1: (R)-4-((1-(benzo[d][1,3]dioxol-5-yl)propan-2-yl)amino)-4-oxobutyl nitrate To a solution of 2-1-4, tert-butyl (R)-(1-(benzo[d][1,3]dioxol-5-yl)propan-2-yl)carbamate (200 mg, 0.716 mmol, 1 equiv) in dichloromethane (3.3 mL), TFA (0.7 mL) was added. It was stirred for one hour and concentrated under reduced pressure. The residue was dissolved in DMF (4 mL), then 4-(nitrooxy)butanoic acid, 2-1-3 (117.43 mg, 0.788 mmol, 1.1 equiv), HATU(408.36 mg, 1.074 mmol, 1.5 equiv) and DIEA (277.62 mg, 2.148 mmol, 3 equiv) was added into the solution. The mixture was stirred for one hour. The residue was purified by reversed-phase flash chromatography with the following conditions: column, C18 silica gel; mobile phase, acetonitrile in water (0.05% NH$_4$HCO$_3$), 20% to 50% gradient in 12 min; detector, UV 220 nm. The eluent was lyophilized. This resulted in (R)-4-((1-(benzo[d][1,3]dioxol-5-yl)propan-2-yl)amino)-4-oxobutyl nitrate, 2-1 (25.7 mg) as a white solid. MS m/z [M+H]$^+$ (ESI):311.10. $^1$H NMR (300 MHz, Chloroform-d) δ 6.79-6.50 (m, 3H), 5.93 (s, 2H), 5.26 (s, 1H), 4.60-4.31 (m, 2H), 4.31-4.08 (m, 1H), 2.76-2.55 (m, 2H), 2.28-2.16 (m, 2H), 2.15-1.92 (m, 2H), 1.12 (d, J=6.6 Hz, 3H). Plasma stability of (R)-4-((1-(benzo[d] [1,3]dioxol-5-yl)propan-2-yl)amino)-4-oxobutyl nitrate, Prodrug 2-1

TABLE 3

Stability of Prodrug 2-1 in Plasma of Different Species

| Compound | Species | T$_{1/2}$ (min) | Remaining Percentage (%) | | | | | |
|---|---|---|---|---|---|---|---|---|
| | | | 0 min | 15 min | 30 min | 60 min | 120 min | 120 min |
| Propantheline | Human | 14.78 | 100.00 | 72.22 | 39.13 | 6.46 | 0.12 | 0.12 |
| Prodrug 2-1 | | 908.64 | 100.00 | 100.94 | 102.03 | 90.66 | 93.79 | 93.79 |
| Lovastatin | Rat | 4.48 | 100.00 | 9.82 | 0.00 | 0.00 | 0.00 | 0.00 |
| Prodrug 2-1 | | 230.30 | 100.00 | 96.93 | 93.53 | 81.00 | 70.84 | 70.84 |
| Propantheline | Mouse | 26.96 | 100.00 | 72.20 | 49.21 | 22.77 | 4.69 | 4.69 |
| Prodrug 2-1 | | 1573.92 | 100.00 | 95.13 | 98.19 | 95.02 | 93.59 | 93.59 |

Propantheline and Lovastatin are reference compounds.

Scheme 3

TABLE 4

Solubility Result of 2-1 and Control Compound in FaSSIF

| Compounds | Solublity (uM) FaSSIF |
|---|---|
| Diclofenace | 285.47 |
| 2-1 | 284.33 |

Diclofenace is a reference compound

Diclofenace is a reference compound

TABLE 5

Stability results of test compound and control compound in PBS pH 6.5, SGF with and without pepsin

| Compounds | Incubation | T$_{1/2}$ (min) | Remaining Percentage (%) | | | | |
|---|---|---|---|---|---|---|---|
| | | | 0 min | 30 min | 60 min | 120 min | 240 min |
| Chlorambucil | PBS (pH 6.5) | 47.72 | 100 | 62.6 | 39.9 | 15.07 | 2.05 |
| Erythromycin | SGF with pepsin | 39.82 | 100 | 59.9 | 39.02 | 12.40 | 1.57 |
| Erythromycin | SGF without pepsin | 40.25 | 100 | 60.53 | 34.86 | 11.45 | 1.64 |
| 2-1 | PBS (pH 6.5) | 802.89 | 100 | 104.05 | 105.81 | 98.20 | 83.83 |
| 2-1 | SGF with pepsin | 811.92 | 100 | 98.88 | 98.96 | 89.53 | 82.75 |
| 2-1 | SGF without pepsin | 858.66 | 100 | 95.42 | 99.51 | 93.54 | 81.87 |

Chlorambucil and Erythromycin are reference compounds.

The invention claimed is:
1. A compound of Formula (I):

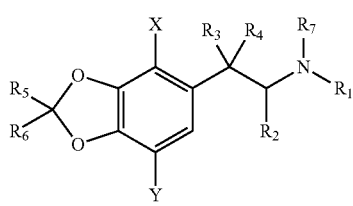

or a pharmaceutically acceptable salt thereof; wherein,
$R_1$ is $-(C=O)(CR_9R_{9'})_n-ONO_2$ or $-(C=O)(CR_9R_{9'})_m-CH(NH_2)CH_2ONO_2$;
$R_2$ is H, $C_1$-$C_4$ alkyl, or $CF_3$;
$R_3$ and $R_4$ are independently H or F;
$R_5$ and $R_6$ are independently H, $C_1$-$C_6$ alkyl, or $CF_3$;
$R_7$ is H or $CH_3$;
$R_8$ is H, $C_1$-$C_6$ alkyl, or $CF_3$;
$R_9$ and $R_{9'}$ are independently H, halogen, or $C_1$-$C_6$ alkyl;
X and Y are independently H, F, Cl, Br, or $OR^8$;
n is an integer from 1 to 9; and
m is an integer from 1 to 9.

2. The compound of claim 1, wherein $R_1$ is $-(C=O)(CR_9R_{9'})_n-ONO_2$.
3. The compound of claim 1, wherein $R_1$ is $-(C=O)(CR_9R_{9'})_m-CH(NH_2)CH_2ONO_2$.
4. The compound of claim 1, wherein $R_1$ is $-(C=O)(CH_2)_m-CH(NH_2)CH_2ONO_2$.
5. The compound of claim 1, wherein $R_2$ is $C_1$-$C_4$ alkyl.
6. The compound of claim 1, wherein $R_2$ is methyl.
7. The compound of claim 1, wherein $R_2$ is $CF_3$.
8. The compound of claim 1, wherein $R_3$ and $R_4$ are H.
9. The compound of claim 1, wherein $R_3$ and $R_4$ are F.
10. The compound of claim 1, wherein $R_5$ and $R_6$ are H.
11. The compound of claim 1, wherein $R_5$ and $R_6$ are $C_1$-$C_6$ alkyl.
12. The compound of claim 1, wherein $R_5$ and $R_6$ are $CF_3$.
13. The compound of claim 1, wherein $R_7$ is H.
14. The compound of claim 1, wherein $R_7$ is $CH_3$.
15. The compound of claim 1, wherein X and Y are H.
16. The compound of claim 1, wherein X and Y are F.
17. The compound of claim 1, wherein m is 2.
18. The compound of claim 1, wherein n is 3.
19. The compound of claim 1, wherein n is 4.
20. The compound of claim 1, having the formula:

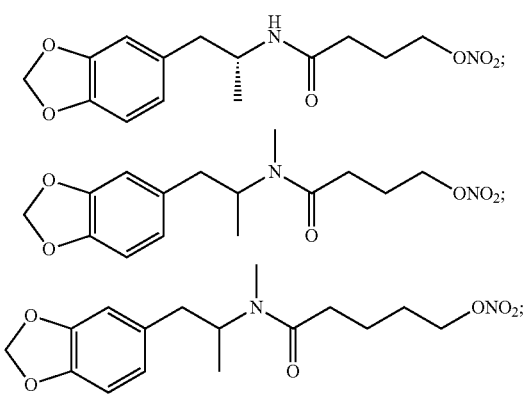

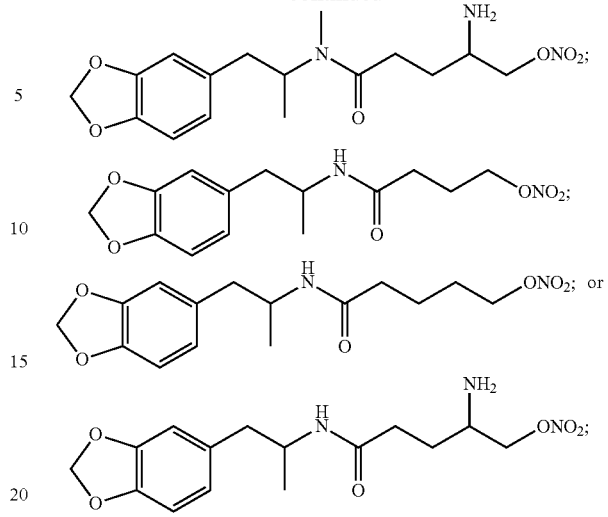

or a pharmaceutically acceptable salt thereof.

21. A compound of Formula (II):

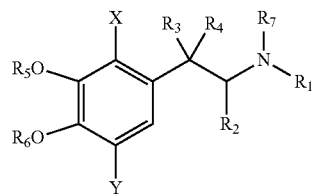

or a pharmaceutically acceptable salt thereof; wherein,
$R_1$ is $-(C=O)(CR_9R_{9'})_n-ONO_2$ or $-(C=O)(CR_9R_{9'})_m-CH(NH_2)CH_2ONO_2$;
$R_2$ is H, $C_1$-$C_4$ alkyl, or $CF_3$;
$R_3$ and $R_4$ are independently H or F;
$R_5$ and $R_6$ are independently unsubstituted $C_1$-$C_6$ alkyl, or $CF_3$;
$R_7$ is H or $CH_3$;
$R_8$ is H, $C_1$-$C_6$ alkyl, or $CF_3$;
$R_9$ and $R_{9'}$ are independently H, halogen, or $C_1$-$C_6$ alkyl;
X and Y are independently H, F, Cl, Br, or $OR^8$;
n is an integer from 1 to 9; and
m is an integer from 1 to 9.

22. The compound of claim 21, wherein $R_1$ is $-(C=O)(CR_9R_{9'})_n-ONO_2$.
23. The compound of claim 21, wherein $R_1$ is $-(C=O)(CR_9R_{9'})_m-CH(NH_2)CH_2ONO_2$.
24. The compound of claim 21, wherein $R_1$ is $-(C=O)(CH_2)_n-ONO_2$.
25. The compound of claim 21, wherein $R_1$ is $-(C=O)(CH_2)_m-CH(NH_2)CH_2ONO_2$.
26. The compound of claim 21, wherein $R_2$ is $C_1$-$C_4$ alkyl.
27. The compound of claim 21, wherein $R_2$ is methyl.
28. The compound of claim 21, wherein $R_2$ is $CF_3$.
29. The compound of claim 21, wherein $R_3$ and $R_4$ are H.
30. The compound of claim 21, wherein $R_3$ and $R_4$ are F.
31. The compound of claim 21, wherein $R_5$ and $R_6$ are unsubstituted $C_1$-$C_6$ alkyl.
32. The compound of claim 21, wherein $R_5$ and $R_6$ are $CF_3$.
33. The compound of claim 21, wherein $R_7$ is H.
34. The compound of claim 21, wherein $R_7$ is $CH_3$.

35. The compound of claim 21, wherein X and Y are H.
36. The compound of claim 21, wherein X and Y are F.
37. The compound of claim 21, wherein m is 2.
38. The compound of claim 21, wherein n is 3.
39. The compound of claim 21, wherein n is 4.
40. A compound of Formula (III):

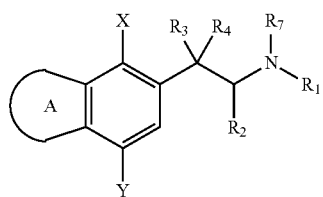
(III)

or a pharmaceutically acceptable salt thereof; wherein, A is

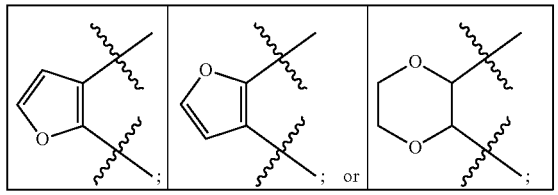 [SMILES: *c1ccoc1* ; *c1ccoc1* ; *C1OCCOC1*]

$R_1$ is $-(C=O)(CR_9R_{9'})_n-ONO_2$ or $-(C=O)(CR_9R_{9'})_m-CH(NH_2)CH_2ONO_2$;
$R_2$ is H, $C_1$-$C_4$ alkyl, or $CF_3$;
$R_3$ and $R_4$ are independently H or F;
$R_7$ is H or $CH_3$;
$R_8$ is H, $C_1$-$C_6$ alkyl, or $CF_3$;
$R_9$ and $R_{9'}$ are independently H, halogen, or $C_1$-$C_6$ alkyl;
X and Y are independently H, F, Cl, Br, or $OR^8$;
n is an integer from 1 to 9; and
m is an integer from 1 to 9.

41. The compound of claim 40, wherein $R_1$ is $-(C=O)(CR_9R_{9'})_n-ONO_2$.
42. The compound of claim 40, wherein $R_1$ is $-(C=O)(CR_9R_{9'})_m-CH(NH_2)CH_2ONO_2$.
43. The compound of claim 40, wherein $R_1$ is $-(C=O)(CH_2)_n-ONO_2$.
44. The compound of claim 40, wherein $R_1$ is $-(C=O)(CH_2)_m-CH(NH_2)CH_2ONO_2$.
45. The compound of claim 40, wherein $R_2$ is $C_1$-$C_4$ alkyl.
46. The compound of claim 40, wherein $R_2$ is methyl.
47. The compound of claim 40, wherein $R_2$ is $CF_3$.
48. The compound of claim 40, wherein $R_3$ and $R_4$ are H.
49. The compound of claim 40, wherein $R_3$ and $R_4$ are F.
50. The compound of claim 40, wherein $R_7$ is H.
51. The compound of claim 40, wherein $R_7$ is $CH_3$.
52. The compound of claim 40, wherein X and Y are H.
53. The compound of claim 40, wherein X and Y are F.
54. The compound of claim 40, wherein m is 2.
55. The compound of claim 40, wherein n is 3.
56. The compound of claim 40, wherein n is 4.
57. The compound of claim 40, wherein A is

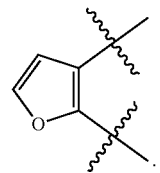 [SMILES: *c1ccoc1*]

58. The compound of claim 40, wherein A is

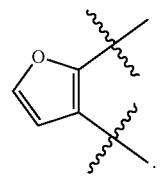 [SMILES: *c1ccoc1*]

59. The compound of claim 40, wherein A is

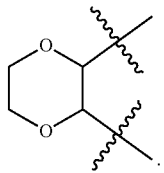

60. A compound having the formula:

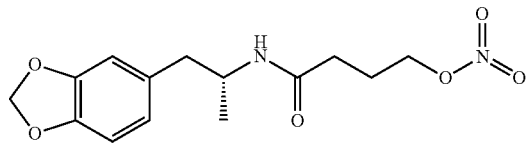

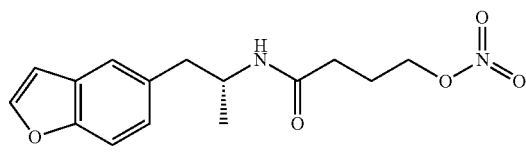

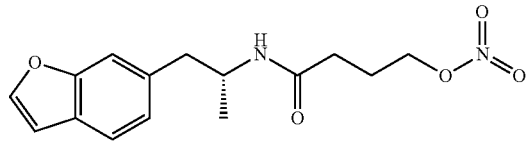

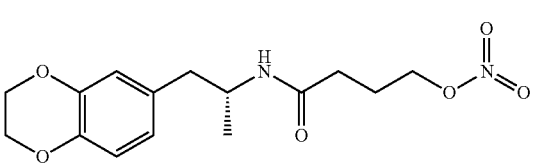

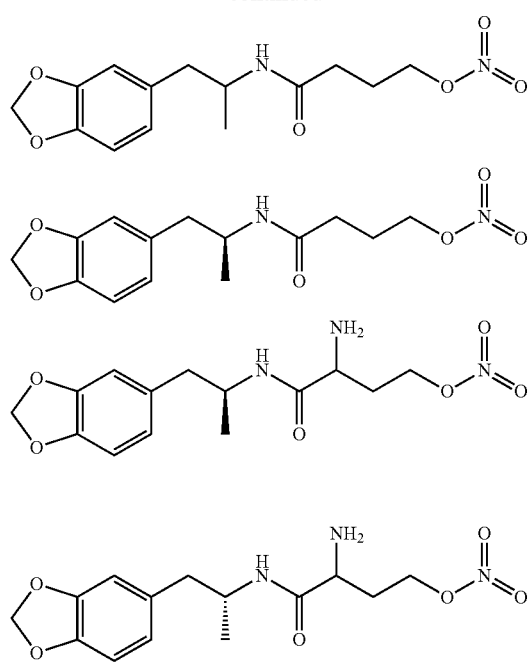
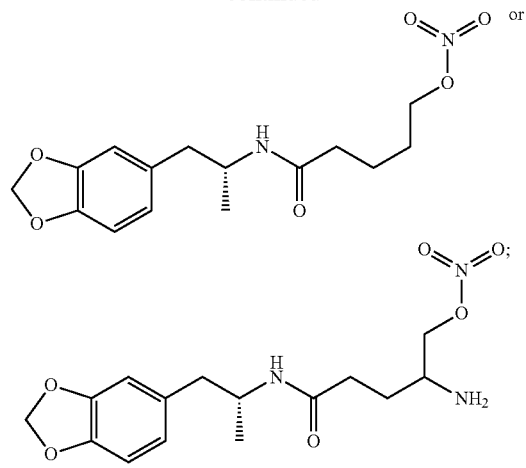
or a pharmaceutically acceptable salt thereof.
61. A pharmaceutical composition, comprising a compound of claim 1 and a pharmaceutically acceptable excipient.
62. A method of treating a mental health disease or disorder, the method comprising administering a therapeutically effective amount of a compound of claim 1 to a patient in need thereof.
* * * * *

UNITED STATES PATENT AND TRADEMARK OFFICE
CERTIFICATE OF CORRECTION

| | | |
|---|---|---|
| PATENT NO. | : 11,912,680 B2 | Page 1 of 1 |
| APPLICATION NO. | : 18/147189 | |
| DATED | : February 27, 2024 | |
| INVENTOR(S) | : Robert B. Perni et al. | |

It is certified that error appears in the above-identified patent and that said Letters Patent is hereby corrected as shown below:

On the Title Page

Item (71), the Applicant listed as "ATAI Life Sciences AG" should be ---EmpathBio, Inc.---

Signed and Sealed this
Seventh Day of May, 2024

Katherine Kelly Vidal
*Director of the United States Patent and Trademark Office*